US009727702B2

(12) United States Patent
Kass-Hout et al.

(10) Patent No.: US 9,727,702 B2
(45) Date of Patent: Aug. 8, 2017

(54) GLOBAL DISEASE SURVEILLANCE PLATFORM, AND CORRESPONDING SYSTEM AND METHOD

(75) Inventors: Taha A. Kass-Hout, Alpharetta, GA (US); Massimo Mirabito, Atlanta, GA (US)

(73) Assignee: Northrop Grumman System Corporation, Los Angeles, CA (US)

( * ) Notice: Subject to any disclaimer, the term of this patent is extended or adjusted under 35 U.S.C. 154(b) by 1083 days.

(21) Appl. No.: 13/280,041

(22) Filed: Oct. 24, 2011

(65) Prior Publication Data

US 2012/0284039 A1    Nov. 8, 2012

Related U.S. Application Data

(62) Division of application No. 12/309,637, filed as application No. PCT/US2006/006758 on Sep. 21, 2006.

(60) Provisional application No. 60/832,954, filed on Jul. 25, 2006.

(51) Int. Cl.
| | |
|---|---|
| G06Q 10/00 | (2012.01) |
| G06F 19/00 | (2011.01) |
| G06Q 10/10 | (2012.01) |
| G06Q 50/22 | (2012.01) |
| G06Q 50/26 | (2012.01) |

(52) U.S. Cl.
CPC ..... *G06F 19/3493* (2013.01); *G06Q 10/1095* (2013.01); *G06Q 50/22* (2013.01); *G06Q 50/26* (2013.01)

(58) Field of Classification Search
None
See application file for complete search history.

(56) References Cited

U.S. PATENT DOCUMENTS

| | | | |
|---|---|---|---|
| 6,766,277 B2 | 7/2004 | Siegel | |
| 7,024,370 B2 | 4/2006 | Epler et al. | |
| 2003/0177038 A1 | 9/2003 | Rao | |
| 2004/0034550 A1 | 2/2004 | Menschik et al. | |
| 2004/0073459 A1 | 4/2004 | Barthell | |
| 2005/0024485 A1 | 2/2005 | Castles et al. | |
| 2005/0055330 A1 | 3/2005 | Britton et al. | |
| 2006/0167735 A1 | 7/2006 | Ward | |
| 2006/0229058 A1 | 10/2006 | Rosenberg | |
| 2006/0271563 A1* | 11/2006 | Angelo | G06Q 10/06 |
| 2011/0004485 A1* | 1/2011 | Sholl et al. | 705/1.1 |

* cited by examiner

*Primary Examiner* — Valerie Lubin
(74) *Attorney, Agent, or Firm* — Andrews Kurth Kenyon LLP; Sean S. Wooden

(57) ABSTRACT

A computer-implemented method for identifying and assessing public health events, and a corresponding system and apparatus, includes capturing public health-related information from structured and unstructured sources, where the information is contained in one or more documents, extracting meta-data from the captured public health-related information, creating an index of the extracted meta-data; archiving the meta-data and the documents, where the index links meta-data to its associated document, processing the extracted meta-data according to one or more detection algorithms to determine if an anomaly exists, and where an anomaly exists, providing a public health event notification, and monitoring and evaluating the responses to the public health events.

18 Claims, 27 Drawing Sheets

Sample alert feed:
```xml
<?xml version='1.0' encoding='UTF-8'?>
<alerts alertType="Avian Flu">
    <alert>
        <guid>c44267e2-2cbe-4d9d-a5ea-bdd1058e5a72</guid>
        <city>Atlanta</city>
        <state>GA</state>
        <diagnosed>100</diagnosed>
        <treated>350</treated>
        <stabilizing>1200</stabilizing>
        <recovering>1200</recovering>
        <recovering>35</deceased>
        <source> </source>
        <comments></comments>
    </alert>
</alerts>
```

GLOBAL DISEASE SURVEILLANCE PLATFORM, AND CORRESPONDING SYSTEM AND METHOD

CROSS-REFERENCE TO RELATED APPLICATION(S)

This application is divisional application of U.S. patent application Ser. No. 12/309,637, filed Jan. 26, 2009, entitled "GLOBAL DISEASE SURVEILLANCE PLATFORM, AND CORRESPONDING SYSTEM AND METHOD," which claims the benefit of PCT Application No. PCT/US2006/036758, filed Sep. 21, 2006, entitled "GLOBAL DISEASE SURVEILLANCE PLATFORM, AND CORRESPONDING SYSTEM AND METHOD" and U.S. Provisional Application No. 60/832,954, filed Jul. 25, 2006, entitled "GLOBAL DISEASE SURVEILLANCE PLATFORM, AND CORRESPONDING SYSTEM AND METHOD," all of which are herein incorporated by reference in their entirety.

TECHNICAL FIELD

The technical field is medical and public health warning and response systems.

BACKGROUND

National, state, and local governments are responsible for safeguarding the health and safety of their citizens. Today, that responsibility means coping with unprecedented public health challenges, from both natural causes, such as the avian flu, and from deliberate attacks, such as bio-terrorism. To meet these challenges requires unprecedented levels of cooperation in and among agencies and organizations charged with protecting the safety of communities. Many of these organizations use either proprietary or incompatible technology infrastructures that need to be integrated in order to provide real-time, critical information for effective event monitoring, early event detection, and coordinated emergency response. Information must be shared instantaneously and among numerous entities to effectively identify and respond to a potential threat or emergency-related event.

Significant efforts are underway along these lines, for example, in the public health and bio-terrorism arena. The Centers for Disease Control and Prevention (CDC) of the U.S. Department of Health and Human Services has launched several initiatives aimed at forming nationwide networks of shared health-related information that, when fully implemented, will facilitate the rapid identification of, and response to, health and bio-terrorism threats. The CDC plans the Health Alert Network (HAN), for example, to provide infrastructure that supports distribution of health alerts, disease surveillance, and laboratory reporting. The Public Health Information Network (PHIN) is another CDC initiative that will provide detailed specifications for the acquisition, management, analysis and dissemination of health-related information, building upon the HAN and other CDC initiatives, such as the National Electronic Disease Surveillance System (NEDSS). Other U.S. government agencies, and international agencies, including the U.S. Food and Drug Administration (FDA), the U.S. Environmental Protection Agency (USEPA), the World Health Organization (WHO), and local affiliates of these organizations (e.g., state environmental protection agencies) are also involved in monitoring the outbreak of infectious diseases, or other medical problems, and limiting the spread thereof.

These agencies have in place a number of other initiatives, including a Nationwide Health Information Network (NHIN), which will allow consumers to directly manage their personal patient information, with each consumer being able to access and review their information online through a personal data access portal while healthcare professionals utilize a separate and distinct portal. Another initiative is the Real-time Outbreak and Disease Surveillance (RODS) system, which is an open source, computer-based public health surveillance system for early detection of disease outbreaks. The RODS system is deployed in more than 18 states, Canada, and Taiwan, and was used during the 2002 Winter Olympics. Hospitals send RODS data from clinical encounters over virtual private networks and leased lines using the Health Level 7 (HL7) message protocol. The data are sent in real time. The RODS system automatically classifies a complaint from a hospital visit into one of seven syndrome categories using specific classifiers. The RODS system also has a Web-based user interface that supports temporal and spatial analyses. The RODS system processes sales of over-the-counter healthcare products, but receives such data in a batch mode on a daily basis. The RODS system has been and continues to be a resource for implementing, evaluating, and applying new methods of public health surveillance. Still other initiatives are; the Laboratory Response Network (LRN), the FDA's Food Safety Network (eLEXNET); the U.S. Department of Agriculture's Food-Net; the U.S. EPA's National Environmental Public Health Network (NEIEN); and the WHO's Global Outbreak and Alert Response Network.

These initiatives define functional requirements and set standards for interoperability of the information technology (IT) systems that hospitals, laboratories, government agencies and others will use in forming nationwide health networks; however, the initiatives do not solve the problems that exist due to the disparate nature of the data used in the initiatives, the differences between the agencies, and the often opposing needs for both security and quick access to data. For example, a single enterprise, such as a hospital, may have several separate database systems to track medical records, patient biographical data, hospital bed utilization, and vendors. The same is true of the government agencies charged with monitoring local, state and national health. In each enterprise, different data processing systems might have been added at different times throughout the history of the enterprise and, therefore, represent differing generations of computer technology. Integration of these systems at the enterprise level is difficult enough; integration on a national or global level is much more difficult. This lack of easy integration is a major impediment to surveillance, monitoring, identification and early detection, real-time event processing, and response planning and evaluation in the public health and bio-terrorism arenas.

SUMMARY

What is disclosed is a method, implemented on a suitably programmed computing device, for identifying and assessing public health events, comprising capturing structured and unstructured public health-related information, wherein the information is contained in one or more information sources; extracting meta-data from the captured public health-related information; and creating an index of the extracted meta-data; and archiving the meta-data and the sources, wherein the index links meta-data to its associated source.

Also disclosed is a global disease surveillance platform, comprising a platform processor, wherein potential public health events are determined and analyzed, and wherein responses to the public health events are monitored; an interface coupled to the platform processor, wherein the interface receives external feeds comprising structured and unstructured data, and wherein meta-data are extracted from the structured and unstructured data, indexed, and related back to the structured and unstructured data; an external services module that provides geo-spatial services; and a storage device, wherein meta-data from the structured and unstructured data, and the structured and unstructured data are stored.

Still further, what is disclosed is an apparatus for managing phases of a public health event, the apparatus including one or more suitably programmed computing devices, the apparatus comprising an interface that receives structured and unstructured data from one or more external data sources, the interface, comprising a data transformation module that transforms data from the structured and unstructured data sources into a schema consistent with that of the apparatus, and a data classification module that that extracts meta-data related to the structured and unstructured data and creates an index of the meta-data back to the meta data's structured or unstructured data; a data store coupled to the interface, wherein the indexed meta-data and the structured and unstructured data are stored; a processing component coupled to the interface, comprising analysis algorithms, the analysis algorithms applied to the meta-data, an alert module, wherein when a threshold, as indicated by application of the algorithms to the meta-data is exceeded, a public health alert is sounded, and access modules that operate to allow real-time access to the structured and unstructured data, and to the corresponding meta-data, wherein a response to the public health event is managed from pre-planning, detection, and response.

Yet further, what is disclosed is a method for managing a response to a public health event during an entire life cycle of the event, the method executed on one or more networked computers, the method comprising receiving information contained in one or more structured and unstructured data sources; initially processing the information, comprising extracting meta-data from the data sources, wherein the meta-data are linked to their corresponding data source, transforming the extracted meta-data, classifying the transformed meta-data, and storing the indexed meta-data and their corresponding data source, wherein the index allows retrieval of the corresponding data source; analyzing the meta-data to determine if a threshold value indicative of a public health event has been exceeded, wherein if the threshold has been exceeded, providing an initial public health event alert, and continuing to collect, process, and analyze information to allow management of the response.

DESCRIPTION OF THE DRAWINGS

The detailed description will refer to the following drawings in which like numbers refer to like item, and in which:

FIG. 7 illustrates a sample alert feed used with the GDSP™;

FIGS. 8-20 illustrate Web pages associated with implementation and operation of the GDSP™.

DETAILED DESCRIPTION

In the public health arena, early event detection and rapid response to disease outbreaks, and bio-terrorism, for example, may hinge on the ability to quickly and easily access disparate sources of epidemiological information, including the ability to exploit non-structured data sources such as Internet free text (e.g., email, blogs). This informational access ensures electronic reporting of clinical syndromes from all possible sources, timely notification of all disease outbreaks of urgent local, national, or international importance, support for outbreak response management, and sufficient input to compatible detection, analysis, visualization, and decision support tools so as to enable prompt situation assessments. Accordingly, a global disease surveillance platform (GDSP™), and a corresponding system and a method for implementing the GDSP™, are disclosed. The GDSP™ can be used to perform powerful multi-lingual disease and outbreak searching across multiple sources; mine disease-related data sources using data and text mining tools; and model and monitor diseases and outbreaks using statistical modeling, On Line Analytical Processing (OLAP), visualization, and mapping tools. Access to the GDSP™ may be made by public health officials, and in some aspects, members of the general public through the Internet.

Figure 1:
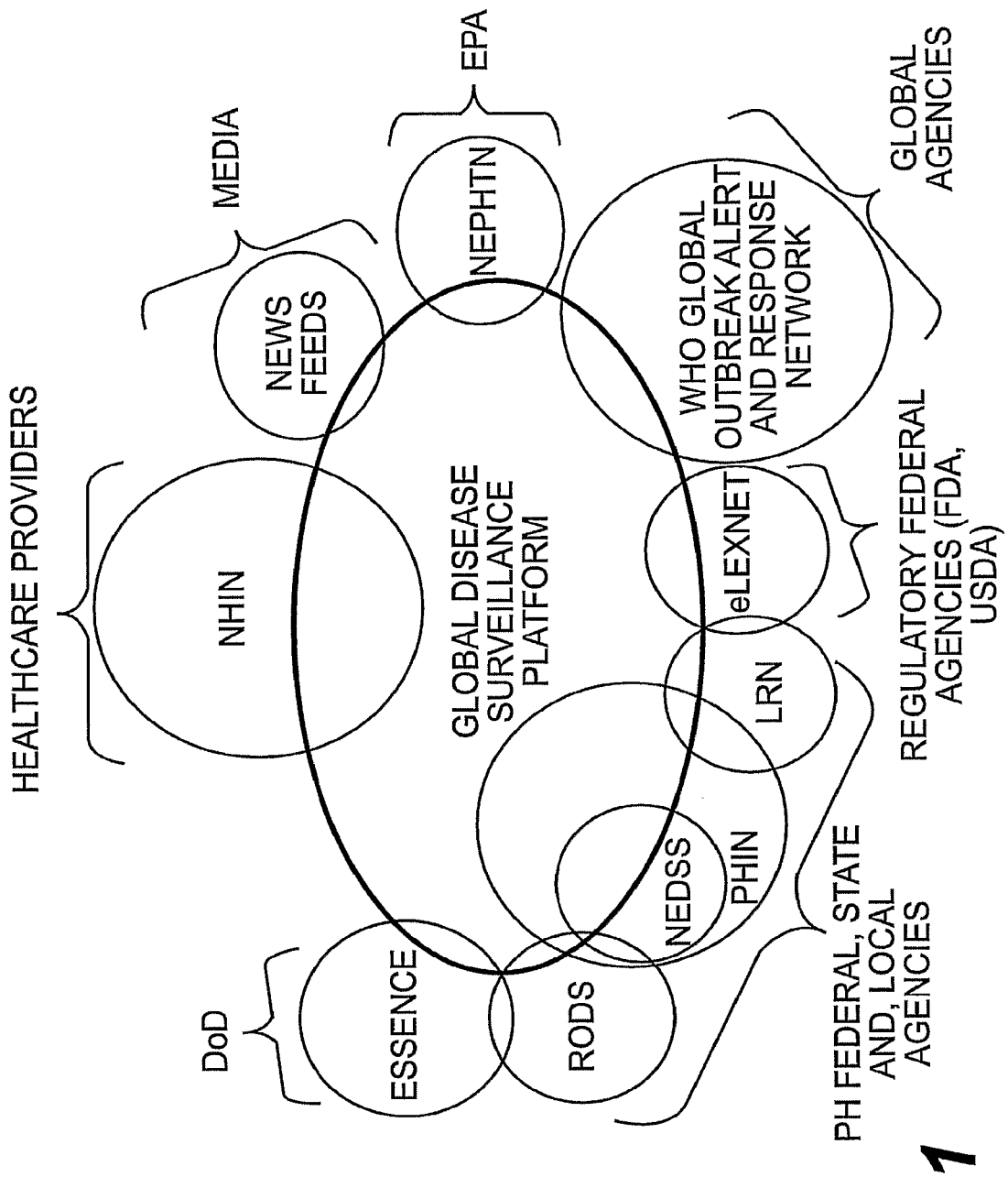
FIG. 1 illustrates governmental and non-governmental agencies and their programs that a global disease surveillance platform (GDSP™) monitors to identify and detect public health problems.

The GDSP™ provides a common set of tools, approaches and data that can be shared at the local, state, federal and international level (see FIG. 1), with the goal of improving the response of the public health community in the area of disease outbreaks, national calamities and pandemics. The GDSP™ aggregates and consumes structured and unstructured health-related data and provides the following high-level functionality:

Data harvesting: The GDSP™ includes components required to extract data from structured and unstructured data sources.

Classification: The GDSP™ provides capabilities to classify information using categories of events.

Fusion: The GDSP™ provides unique capabilities to merge structured and unstructured data and linking, categorizing and ranking information.

Search and filtering: The GDSP™ provides capabilities for users to search, mine and filter data.

Alert notifications: The GDSP™ provides an early warning mechanism based on user-defined thresholds.

Output: The GDSP™ provides support for reporting, visualization, temporal analysis and data export.

Restricted access: The GDSP™ provides secure communications access to partners using the GDSP™

Public access: The GDSP™ provides anonymous access to non-sensitive information.

Response planning and monitoring: The GDSP™ provides users and public health officials with the tools to plan for potential public health events and to manage the response to an event throughout the event's life cycle.

The GDSP™:

Enables multidisciplinary collaboration among global, national, state and local public health agencies, community hospitals, academic health centers, community healthcare providers, laboratories, professional societies, medical examiners, emergency response units, safety and medical equipment manufacturers, the media, government officials, and federal agencies such as the U.S. Office of the Assistant Secretary for Public Health Emergency Preparedness, CDC, and the Agency for Toxic Substance and Disease Registry (ATSDR).

Identifies, based on specific criteria, emerging and re-emerging public health events, allows close monitoring of unexplained morbidity and mortality due to public health events, such as infectious diseases, and provides for better surveillance for flu-like illness.

Establishes communication linkages with laboratory response networks for a rapid evaluation and identification of public health event agents such as bio-terrorism agents.

Allows the medical community to collaboratively share, develop, and activate diagnostic clinical and treatment protocols, which are communicated to the medical community and which improve rapid and early detection and reporting of suspect cases, unusual clusters of disease, and unusual manifestations of disease.

Provides for public health planning for and response, where necessary, to reduce the morbidity from the public health event by viewing the status of stockpile of antibiotics, communicating and preparing multilingual patient information, collaboratively developing contingency plans for quarantine, and collaboratively developing and communicating community plans for the delivery of medical care to large numbers of patients and to the "worried well."

Use and expansion of access to health alert networks.

Collaboratively developed contingency plans, with local medical examiners, for mass mortuary services, including plans for the utilization of Federal Disaster Medical Assistance Teams (DMAT) and Mortuary Teams (DMORT).

Provides for training, by Communities of Interest, of health organizations that deliver care.

Communicates emergency instructions, prevention, control and treatment information.

Helps resolve legal issues related to public health authority in emergencies.

Figure 2:
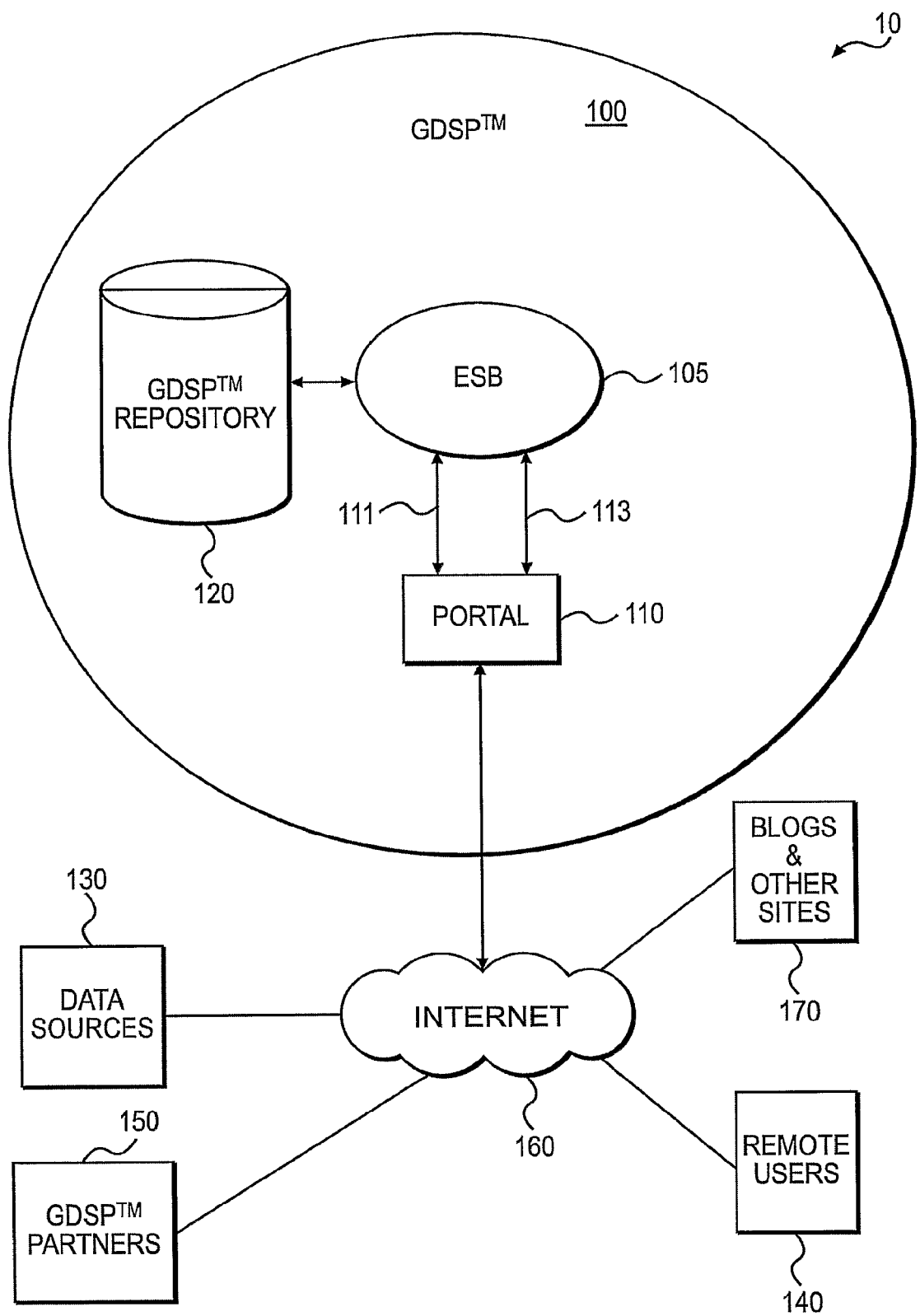
FIG. 2 illustrates an environment in which the GDSP™ operates, and illustrates major components of the GDSP™.

FIG. 2 is an overall diagram of a global disease surveillance platform (GDSP™) 100 as it relates to various government and non-government agencies in the public health and bio-terrorism arenas. The GDSP™ 100 exists as part of a global disease surveillance environment 10, and includes enterprise service bus 105 and portal 110, through which processing components of the GDSP™ 100 are accessed; and global disease information repository 120, where critical data needed to operate the GDSP™ 100 and to provide the functionality listed above may reside. Coupled to the GDSP™ 100 are data sources 130, which provide the critical public health data consumed by the GDSP™ 100, and remote users 140, who access the GDSP™ 100 through secure path 111 or unsecure path 113, to gain access to the data and products of the GDSP™ 100; GDSP™ partners 150, which provide the data sources 130, and which receive outputs from the GDSP™ 100; and other data sources 170, such as media services, emails, and blogs. The various remote users 140, and the GDSP™ partners 150, may be linked together over a data network, such as the Internet 160, for example. The users 140 and the partners 150 may interact with the GDSP™ 100 through queries, by subscription, on a transactional basis, and/or through multi-party collaboration hosted within the GDSP™ 100.

The data sources 130 and 170 may include any data source capable of transmitting digital information. Examples of such data sources include SQL data, SQL data via JDBC, flat files, XML, XML Web Services Description Language (WSDL) files, and ANSI EDI files; email, RSS feeds, web service WSDL enabled applications; and SQL data sources. One of ordinary skill in the art will recognize that many other types of data sources may communicate and work with the GDSP™ 100. The data sources 130 and 170 may be maintained at one or more external partners 150 in the system 10. Access to the data sources 130 and 170 may be permitted under an agreement between an external partner 150 and the GDSP™ operators. Other data sources 130, 170 may be freely accessed over the Internet 160. Data in the data sources 130 may be structured, and may be compatible with the schema employed by the GDSP™ 100. Alternatively, the data may be unstructured, and may require mapping to the schema used by GDSP™ 100. Here, unstructured data refers to masses of (usually) computerized information that do not have a data structure which is easily readable by a machine. Examples of unstructured data may include audio, video and unstructured text such as the body of an email or word processor document. The data in the data sources 170 typically will be unstructured.

The data sources 130 include external partner data feeds. The external partner data feeds may be provided electronically in digital format expressed as spread sheets, XML documents, CSV documents, email, RSS feeds, and SQL queries, for example. The external partner data feeds may be provided periodically, on-demand, or a combination of periodically and on-demand. The external partner data feeds may include medical data, patient data, environmental data, hospital utilization data, and any other data needed to monitor and control public health. The external partner data feeds are provided to the GDSP™ 100, and may be stored in their original format in external system databases or in the data repository 120, awaiting processing in the GDSP™ 100. Unstructured data derived from the external partner feeds are processed, tagged with meta-data, indexed, and linked to similar content. Structured data are mapped to the GDSP™ schema using components of the GDSP™ 100.

Figure 3A:
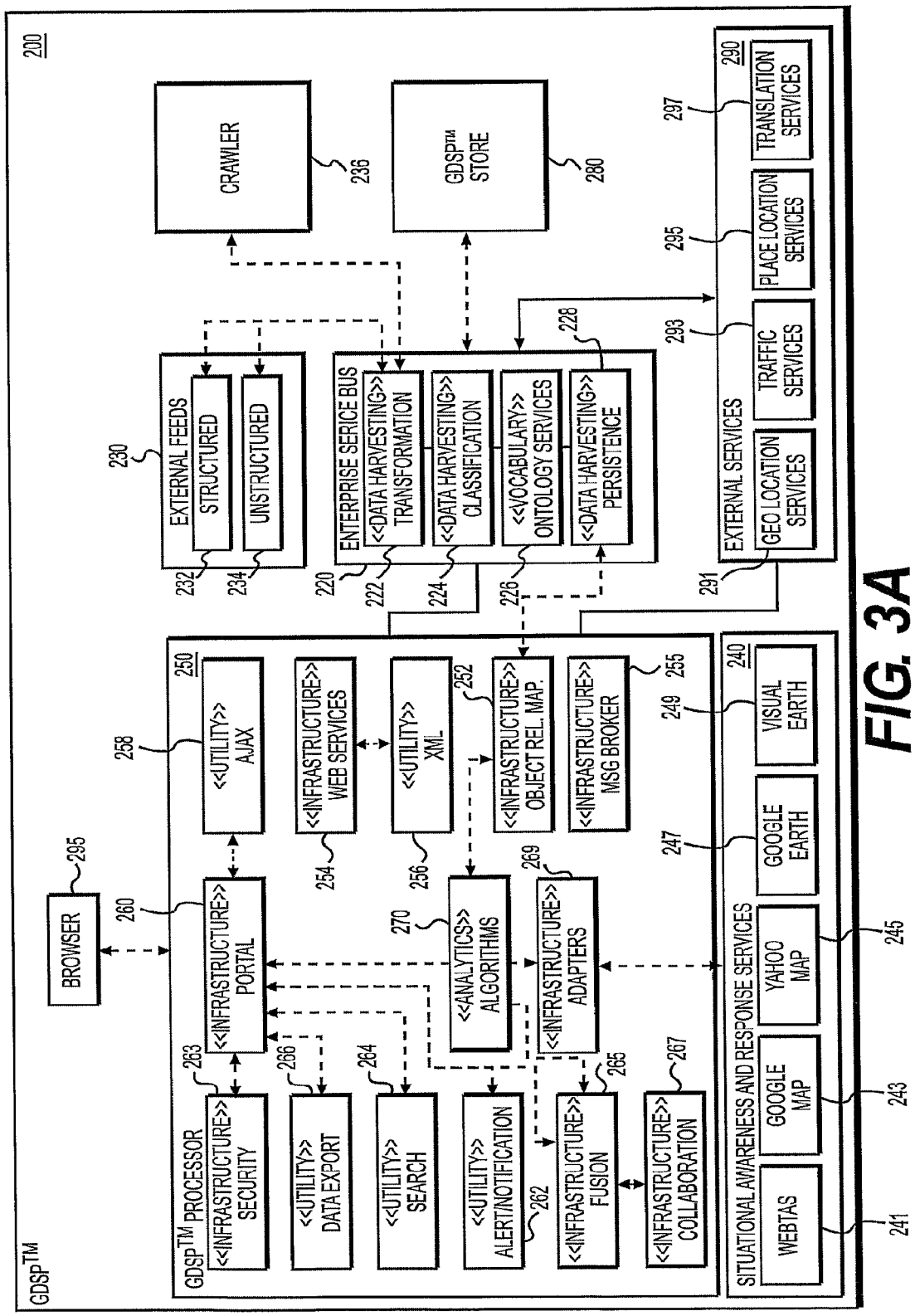
FIGS. 3A-3C are architectural diagrams of the GDSP™.
Figure 3B:
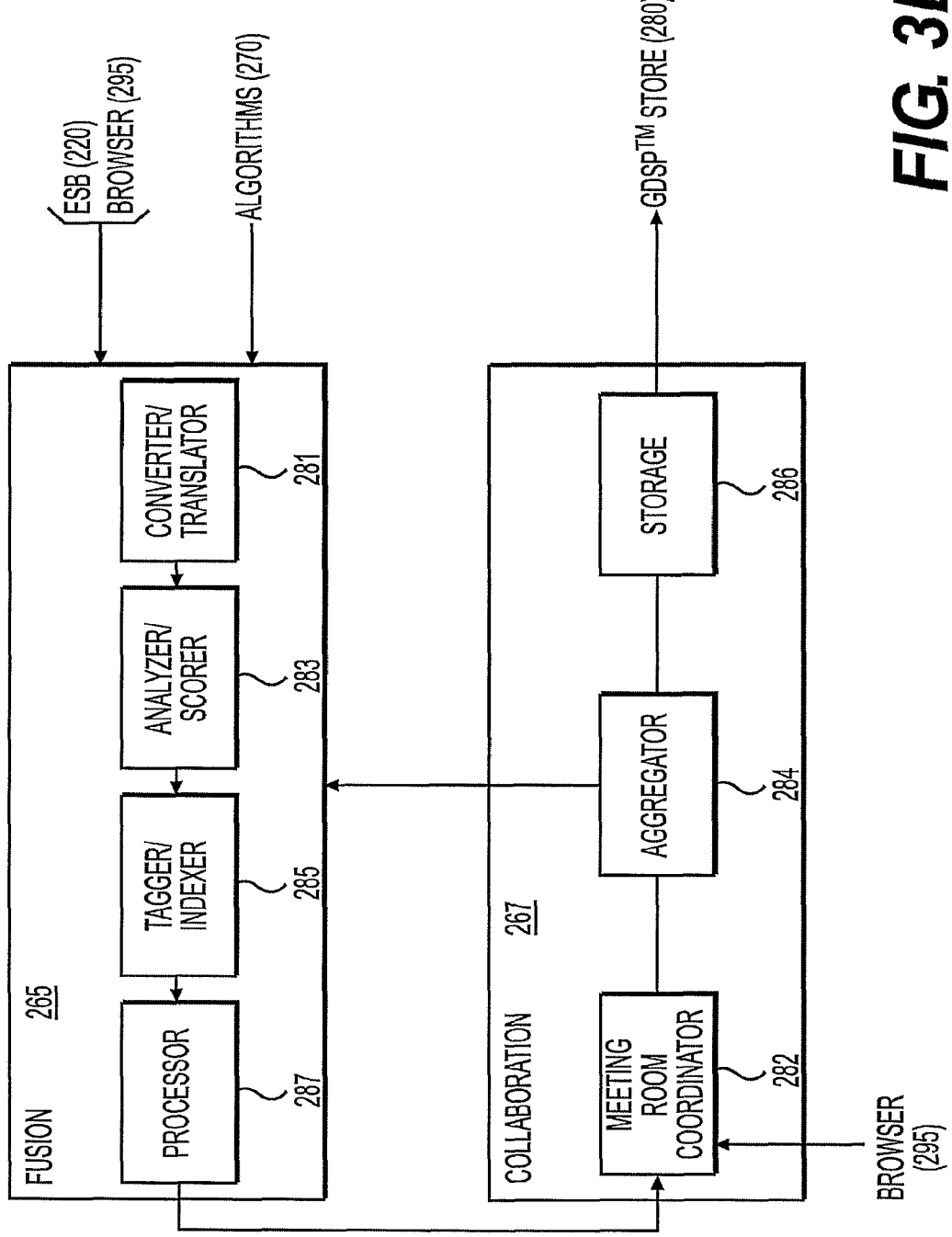
Figure 3C:
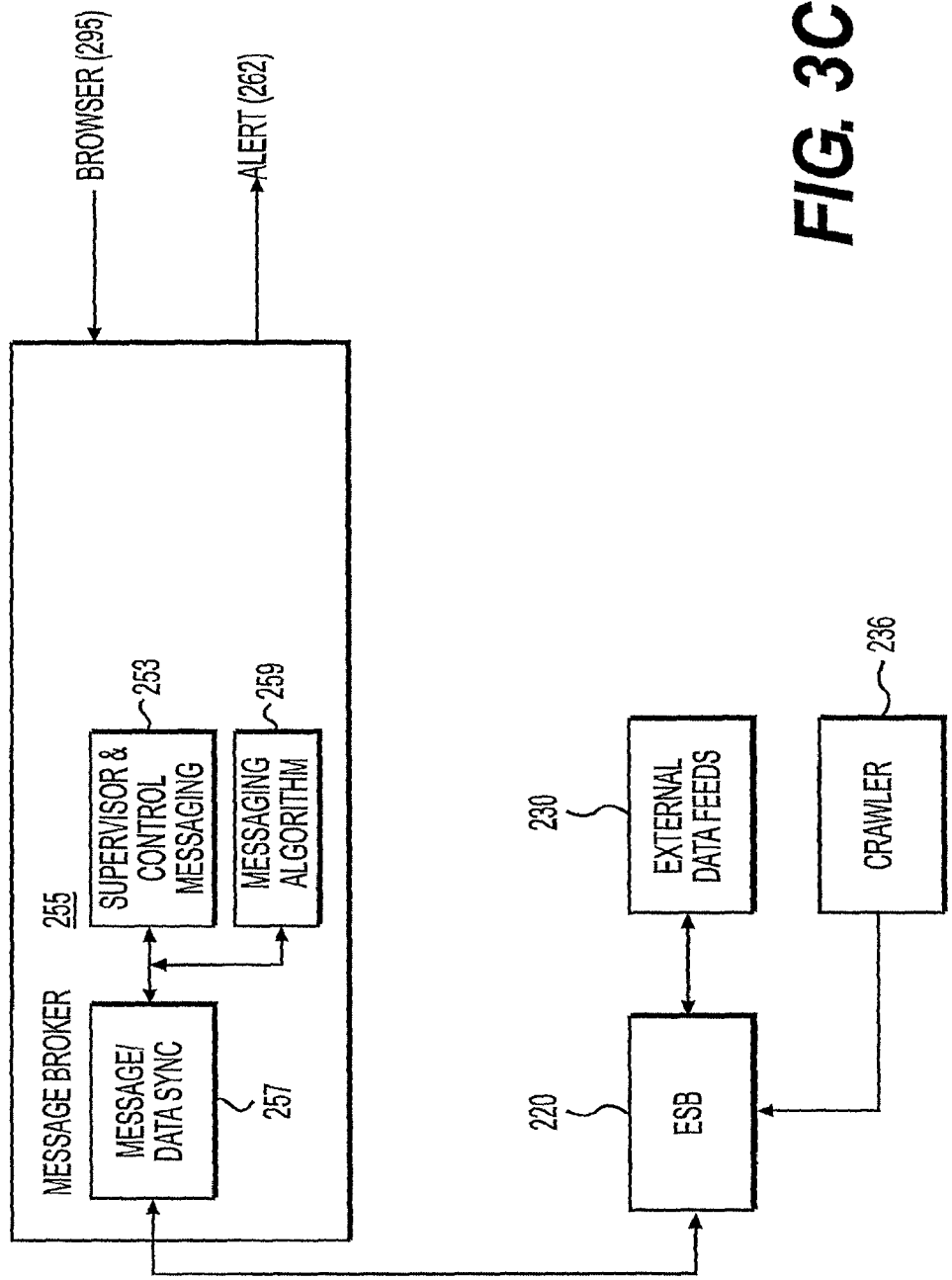

FIGS. 3A-3C are diagrams of an architectural plan of the GDSP™ 100. FIG. 3A is an overall block diagram of an architectural plan 200 of the GDSP™ 100, showing selected components thereof. The architecture 200 may be installed on a networked server, which may be accessible by other network devices. Alternatively, elements of the architecture 200 may be installed on other network devices, or local terminals, that are coupled to the networked server. The other network devices may use the architecture 200 to obtain various views of the GDSP™ process. The other network devices may include a personal computer or a handheld device, for example, and an operator (i.e., human) of the personal computer or the handheld device may use the architecture 200 to obtain a desired view (e.g., avian flu vaccine shipment status) of the GDSP™ process. Another network device may query the architecture 200, without direct human direction or intervention, to obtain information related to the GDSP™ process, for example, by using RSS feeds or a REST API.

The architecture 200 includes components that serve as means for interfacing with external feeds 230 and crawler 236 to access data from these data sources, translating the data into a schema used in the architecture 200, and formulating and executing queries of the data. The architecture 200 includes means for the mapping data sources into the GDSP™ schema. Also included in the architecture 200 are means for providing security for transactions involving the external feeds 230. The architecture 200 further includes means for controlling messaging between the architecture 200 and the external feeds 230. The architecture 200 still further includes means for viewing, analyzing, processing, and storing data from the data sources. Finally, the architecture 200 includes means for executing queries of the processed data from the data sources, as well as the raw data contained in the data sources.

An Enterprise Service Bus (ESB) 220 forms the backbone of the GDSP™ architecture 200. The ESB 220 provides an abstraction layer for message routing, transaction management and application integration, and couples a GDSP™ store 280, the external feeds 230 and the crawler 236, external services module 290, and processing components 250. The processing components 250 also receive inputs from situational awareness module 240, and directly from the external services module 290 (translation services module 297, place location services module 295, traffic services module 293, and geo-location services module 291). Finally, the processing components 250 may be accessed through a browser 295, which may be a standard Internet browser residing on a computing platform of one of the remote users 140.

Data acquisition services are a key element of the GDSP™ 100. To access the information from the external feeds 230 on a real-time, on-demand basis, the architecture 200 may be used to determine a schema related to data from each of the data sources 232, 234, 236 and to map the data to a schema within the architecture 200. To accommodate this mapping, the architecture 200 includes data acquisition, evaluation, and synchronization functions. These functions may be realized by use of an established schema, for example, to which the data in one or more of the data sources 232, 234, 236 are mapped. More specifically, data harvesting components 222 (transformation), 224 (classification), 226 (ontology), and 228 (persistence) within the ESB 220 are used to extract data from structured (232) and unstructured (234, 236) data supplied by the external feeds 230 and the crawler 236, and then pass the harvested data to the processing components 250 of the GDSP™ architecture 200. The GDSP™ 100 can harvest data using pull or push services. Pull services require the GDSP™ 100 to periodically initiate data access functions while with push services, the GDSP™ 100 passively waits for incoming information. In both cases, once a data target has been identified, the data target will be transformed (harvesting component 222) and routed to the appropriate GDSP™ components 224, 226, and 228 for further processing. Each component 222, 224, 226, and 228 is deployed as a plug-in. Since each data feed will have unique characteristics, new plug-ins can be registered into the GDSP™ architecture 200, thereby providing data flexibility, customization and independence. Both the harvested data and the original (raw) data may be persisted into the GDSP™ store 280.

For unstructured information like free-text or derived reports, the GDSP™ 100 mines the Web (both publicly accessible sites as well as partner sites that require authenticated access) based on predefined algorithms/set of rules for standard key words, such as those in the Unified Medical Language System (UMLS), and/or a particular concept. Once a data source is found, that source's raw information will be cached and stored in the GDSP™ 100 with a reference link mapping to the data source; categorization of the data is also applied to the raw data based on pre-defined ontology services 228. Classification service 224 further assesses the information based on discovered relationship(s) with other concepts or documents using a real-time scoring algorithm as part of the ESB 220. For example, mining ProMED listserv email for H5N1 Avian influenza/bird Flu, a GDSP™ service agent (not shown) will scan every email looking for UMLS keywords. Once a target data source is acquired by the ESB 220, the data source is cached and persisted (228) in the GDSP™ store 280, and this process continues for all the target documents. Parallel to this process, each acquired document will be tagged/indexed with one or more predefined categories in 226 for further correlation. A GDSP™ user on the front end (i.e., at 140/150—see FIG. 2) may access this categorized and cached information using the portal 260.

For semi- or highly structured information 232 the GDSP™ 100 may import the information into a predefined table schema. For example, WHO avian flu reports are semi-structured with information on location, gender, pathogen type, route of transmission, total fatalities and cases, etc., which can be scrubbed and loaded into a predefined table schema in the GDSP™ store 280.

As noted above, the external feeds 230 can supply structured data 232 and unstructured data 234 to the GDSP™ 100. The GDSP™ 100 may also use a data acquisition device, such as the crawler 236, to access the Internet in search of various (mostly unstructured) data sources. The crawler 236 operates on a continuous basis. The crawler 236 is programmed to search for data sources related to public health and bio-terrorism, world wide. Such programming may include use of key words, including the UMLS, for example. The crawler 236 may also be programmed to "learn" new search criteria. For example, the crawler 236 may return an unstructured data source based on UMLS key word searching. The crawler 236 may identify other terms in the data source, and may use these new terms for subsequent Internet searching. Alternatively, the crawler 236 receives "feedback" from the ESB 220, such as meta-data extracted from the sources 232, 234, and uses the feedback as a basis for future searching. For example, if the meta-data from an information source includes a specific Web address, the crawler 236 may look for all further data sources having the same Web address. Other algorithms may be incorporated into the crawler to facilitate comprehensive and efficient Internet searches.

Data fusion components allow the GDSP™ 100 to automatically analyze structure and unstructured data in 230 and link similar data together. Data fusion components also allow the GDSP™ user/analyst to effectively review a wide range of data sources. Some aspects of data fusion reside in the ESB 220 (information sources 232, 234 feeding into ESB components 222, 224, 226, and 228), while others reside in fusion module 265, which will be described in conjunction with FIG. 3B. Data fusion provides a holistic view into the data platform and gives the GDSP™ user an opportunity to review and consume a variety of data points. Data fusion components within the ESB 220 provide more comprehensive picture of the data by merging information from disparate sources (the external feeds 230, for example) despite differing conceptual, contextual and typographical representations as means for consolidating data from structured or unstructured resources. For example, a ProMED email alert concerning avian flu in Thailand might consist of free text with parameters on the location, transmission route, age, etc. of a suspect case in one region. At the same time a video stream as well as news feeds from the media and blogs may report the incident. Looking at these sources of information separately may not alert an analyst, or cause an automated alert; however, when these sources of information are put together, using the ESB 220 components, the "fused" information sources may point to the single location (as processed by configurable geo-coding service 291) in one point in time. Such a congruence of data feeds could indicate an anomaly, which could trigger an automated public health alert (alert module 262), and/or which would help the GDSP™ decision maker/analyst gain a cohesive picture of the threat and be able to orchestrate a coordinated response using GDSP™ tools. (Examples of such tools are those provided in situational awareness and response services component 240, including WebTAS 241, Google Maps 243, Yahoo maps 245, Google Earth 247, Visual Earth 249, and the collaboration service 267.) In addition, the ESB 220 brokers requests between the GDSP™ 100 and external services 290, such as Place Location Services 295 (e.g., nearby hospitals, fire departments, pharmacies, police stations, hospital capacity, etc.), by accessing Yahoo services using a REST API.

The ESB 220 also allows subscribers in 140 and 150 (see FIG. 2) to automatically receive information using Web services component 254 (available via a REST API, RSS), or to manually extract data using data export component 266. This enables further analysis by GDSP™ users employing their own classification and analysis tools beyond what is provided in the GDSP™ architecture 200.

Once transformed into the data schema used by the architecture 200, the data are classified, using classification component 226, which adds, for example, meta-data tags to each data point, indicating how the data may be used, its "shelf life," access requirements, and other information. The classified data are then passed to the persistence component 228 for eventual storage in the GDSP™ store 280.

Within the processor 250, the XML utility 256 is used to read an XML document, or data source, in one format, and transform that document into another XML formatted document as well as to provide the ability to query information in an XML source. For example, an external service in 240 or 290, like Yahoo traffic, Yahoo places, or Yahoo geocoders, provides information in a specific XML format, which then needs to be transformed by XML utility 256 using, for example, the APACHE digester (based on certain rules) into a list of traffic objects (traffic POJO class). The traffic POJO list is subsequently fed into a transformation object in the XML utility 256 that will transform the JAVA object into an XML stream compatible with the maps in Google Maps component 243. Upon completion of this transformation, the Google XML formatted data is sent back to the browser 295 and used by an API within the Google Map component 243 to overlay markers on a map. For example, this process can be used to display nearby hospitals and their capacity at a certain location where a potential public health event exists.

The various services that constitute the data sources 230 may include security measures to, for example, limit access to data and processes used by the services. For example, an external partner 150 may use an application that incorporates various security measures. The architecture 200 may use these security measures when managing access to data from the external partner's data source. Alternatively, the architecture 200 may provide security measures. For example, the security adapter 263 may limit access to query data from a specific data source to only those individuals or machines that possess a specific password and log-on name.

The security adapter 263 may establish role-based access such that, for example, an organization's managers would be able to access certain medicinal data, but would not be able to access certain patient data, which could be restricted to the organization's medical services personnel. The security adapter 263 can implement access restrictions based on a user's identification as a "normal user" or as a "system administrator." The security adaptor 263 also supports multiple clients and multiple projects within a client.

The GDSP™ 100 provides for automated and manual (i.e., human) detection and analysis of a potential public health event. To execute this function, the GDSP™ includes various algorithms (algorithm component 270 shown in FIG. 3A) that can be applied (automatically or manually) at different points over the life cycle (i.e., from outbreak to termination) of the potential public health event, depending on the characteristics of the event. Some of the most useful algorithmic approaches involve multivariate and univariate time series algorithms, which include CuSum with EWMA, recursive least squares, Wavelet, and simple moving average. In addition, the GDSP™ 100 uses Bayesian analysis as a means to provide early disease detection. Bayesian analysis computes the probability that an event such as an outbreak is taking place based on related information that is evolving in time. Analysis has shown that outbreak detection is more reliable when several different factors increase together, even if none of the factors individually exceeds a particular response threshold, because when only a single factor "spikes," that factor often represents only outlier data. As used in the GDSP™ 100, Bayesian analysis can routinely fuse heterogeneous data by discovering and quantifying the hidden relationships among the data. This also allows the GDSP™ 100 to create and deploy increasingly sophisticated algorithms that take other algorithms as input.

Another tool used in the GDSP™ 100 is cluster detection. A cluster is an increased density (incidence) of cases in time or space.

The time series algorithms used in the GDSP™ 100 provide associated data caching schemes for both data and graphs that serve a large number of simultaneous Web-based users, each of whom simultaneously may request multiple graphic displays at a time. These algorithms are described below:

1. CuSum-EWMA: CuSum is a class of algorithms that can detect gradual changes in the mean and/or standard deviation of a time series by forming cumulative sums from the prediction errors. CuSum implementation uses an exponentially weighted moving average (EWMA) to predict the next value in a time series. As implemented in the GDSP™ 100, a user-specified threshold value and a standard CuSum procedure on the forecast errors are used to determine whether to generate a public health alert. The value of the threshold line is computed by calculating the minimum value that would induce an alert under the above CuSum procedure. The algorithm generates an alert when the cumulative sum exceeds the threshold.

2. Moving Average: The Moving Average algorithm predicts the next value to be the average of the previous [W] values in the time series, where [W] is the window size. The prediction error is computed by subtracting the predicted value of the time series from the observed value. As implemented in the GDSP™ 100, the algorithm generates a public health alert when the prediction error exceeds a threshold based upon historical data. The value of the threshold line on day [d] of a time series is determined by first computing a forecast for day [d] by averaging the data for a preceding period (e.g., for the preceding 30 days). Then, historical forecasts for the 90 days (assuming use of the preceding 30-day period) that precede day [d] are computed using a 30-day average for each forecast. Next, the historical forecast errors are computed by subtracting the forecast from the actual value. Finally, the value of the threshold line on day [d] is computed.
3. Recursive Least Squares: The Recursive Least Squares (RLS) algorithm uses linear regression to construct a forecast for day [d] of a time series. The regression model is similar to an Auto Regressive Integrated Moving Average (ARIMA) model that incorporates auto-regression, 7-day differencing, and a 7-day moving average to produce forecasts. Historical forecast errors are computed by subtracting the forecast from the actual value, and computing the threshold line on day [d]. As implemented in the GDSP™ 100, the RLS generates an alert when the prediction error exceeds a threshold based on the historical data.
4. Wavelet: The wavelet-based anomaly detector (WAD) is designed to detect abrupt changes in a time series by using the wavelet transform to remove short and long-term trends from the time series. The resulting smoothed time series are used to produce forecasts. Historical forecast errors are computed by subtracting the forecast from the actual value, and computing the threshold line on day [d]. As implemented in the GDSP™ 100, the WAD generates an alert when the wavelet prediction error exceeds a threshold based on historical data.
5. Bayesian Spatial Scan Statistic Algorithm: As implemented in the GDSP™ 100, a spatial scan statistic (SSS) algorithm searches a geographic region [R] for a subregion [S] that has an unexpectedly high count of some quantity of interest. One such quantity would be the number of reported cases of salmonella food poisoning by location (e.g., by zip code). The search is performed over shapes of a particular type, such as circles, ellipses, or rectangles; for a given type of shape, many sizes of that shape are considered. By implementing a branch-and-bound search technique, the normal time to find the subregion [S*] that is most likely to contain an outbreak will decrease by about a factor of 1000. When executed, this Bayesian algorithm is about one million times faster than conventional algorithms that perform a corresponding outbreak detection task.

Additional algorithms may be included, such as the Bayesian Aerosol Release Detect (BARD) algorithm developed by the University of Pittsburg RODS laboratory, to support criminal and epidemiological investigations. This algorithm type supports event reconstruction and analysis, which, particularly in a bio-terrorism scenario, may assist law enforcement (as well as epidemiological) investigators catch the event perpetrators before they can strike again. This model analyzes emergency room complaints and meteorological data to compute a posterior probability of, for example, anthrax release, release time, release location, release quantity, and number of affected individuals. The model is akin to an "inverse plume" model, in that the model can take casualty number and location data and calculate the approximate time, place and amount of a deliberate infectious but non-contagious aerosol pathogen release. The model combines the Gaussian atmospheric dispersion model with a Bayesian network. The Bayesian network represents knowledge about the relationship between observable biosurveillance data, disease parameters, and exposure to aerosolized biological agents. The method can also be applied to other types of biosurveillance data including results from BioWatch monitoring (an early warning program intended to detect the release of biological agents within 36 hours of their release).

Furthermore, capturing normal behavior traits using mathematical methodology establishes patterns that, when violated, may indicate anomalous behavior. Belief Networks (BNs) develop a context sensitive characterization of normal and abnormal activity and provide a probabilistic assessment, with the understanding that some false positives are generated, in order to ensure that true threats are not overlooked. To meet this objective, the GDSP™ 100 exploits strengths of the ability to support hybrid BNs that fuse ensembles of Bayesian BNs, Dempster-Shafer BNs, and other probabilistic reasoning machinery to process observations in the context of knowledge. The result is a probabilistically ranked threat list that is used to search for new hypotheses and to task for the "best next observations" to explain anomalous behaviors.

Finally, the GDSP™ 100 allows analysts the ability to codify their heuristic "rules of thumb" as detection algorithms, which can be captured in the logic of a commercial business rules engine product. These "rules of thumb" can identify potential threats that are best characterized by logical conditions rather than mathematic analysis.

FIG. 3B is a block diagram of the architectural features of fusion module 265 and collaboration module 267. As shown in FIG. 3B, the fusion module 265 receives data from the ESB 220 data from the sources 232, 234, 236—see FIG. 3A) and the browser 295 (by way of portal 260—see FIG. 3A). The fusion module 265 may also receive inputs from the algorithms module 270. If the received data are not already converted/transformed to the schema used by the GDSP™ 100, that processing takes place in sub-module 281. Furthermore, unstructured data (e.g., email) is converted to a consistent format used by the GDSP™ 100. Such conversion may be executed by a translation algorithm that comprises the sub-module 281. Next, the data are analyzed (if not already completed) by analyzer/scorer sub-module 283 according to a set of criteria such as the presence of specific key words that are universally recognized as pertaining to a specific public health event (e.g., avian flu; anthrax; e. coli). The data are also scored based on the relevancy and accuracy of the information contained in the specific data source. For example, a pathology report from an accredited hospital may score higher, and may be considered more accurate, than a news report from a media outlet. Furthermore, the same pathology report would likely be considered more relevant to the determination of a public health event than would a general news article about the same public health event, in that the pathology report contains more directly pertinent and specific data and represents the real-time observations of a public health professional, while a news report is generally a distillation of facts written and targeted to appeal to persons of limited education. Scoring algorithms within the sub-module 283 are able to discern inconsistent "facts" stated in an information source: for example, an incorrectly stated pathway for a biological agent may cause the supplying information source to scored with a lower accuracy than if the pathway was correctly stated.

After analysis and scoring, the information is processed by tag/index sub-module 285 that adds, if not already present, temporal and geo-spatial information to the information. The sub-module 285 also assigns an index number, if not already assigned, which serves to identify the processed information and as a reference to the original, unprocessed information source. The tagged and indexed information is stored in the GDSP™ store 280. The processor sub-module 287 receives the indexed and tagged data, along with the score assigned to the data. A triggering algorithm in the sub-module 287 determines if the data should receive an analyst's review, and the urgency of that review. For example, if the score exceeds an alerting threshold, the sub-module 287 may flag the data for human review, and may send the data (by, for example, email) to one or more GDSP™ analysts. Alternatively, just the data's index may be sent. The processor sub-module 287 also compares the meta-data extracted from the information source, and determines if the information source relates to an existing public health event, or should be assigned to a new public health event. If the information source is to be assigned to an existing public health event, the data's index may be appended to indicate the identity of the appropriate, existing public health event. If the information source does not appear to relate to an existing public health event, then one of two steps is completed. If the information source is scored sufficiently highly, then a new, provisional, public health event may be created, and the information source appended with a corresponding event identifier. If the information source does not score high enough, the information source may be placed in a holding register, awaiting the receipt of additional information sources that appear to relate to a common event.

Following processing by the fusion module 265, the data is next routed to collaboration module 267, where the data is made available to GDSP™ users. In one embodiment, the data is presented to a virtual meeting room, using meeting room coordinator sub-module 282. More specifically, data from a specific information source that is identified as relating to an existing public health event is provided to a meeting room established in the GDSP™ 100 to help manage the response to that event. Once the analyzed, scored, tagged, indexed, and identified data is provided to the meeting room, that data is available to any GDSP™ user who is able to access the specific meeting room (meeting rooms may be password protected, for example). Following assignment to a meeting room (if appropriate), the data is processed by aggregator sub-module 284, which compiles all the related data into a single file for eventual storage (sub-module 286) in the GDSP™ store 280. Note that GDSP™ users may introduce new data sources into the meeting room. The aggregator sub-module 284 processes this new data so that it is properly identified with the other data assigned to the meeting room. The aggregator sub-module 284 may also provide this additional information to the fusion module 265 for analysis and scoring. Additionally, the GDSP™ users may perform various analyses, write notes or comments, or otherwise interact with the data assigned to the meeting room. The aggregator sub-module 284 ensures that any of these data elements are properly related, and stored with other data related to the specific public health event. In the case in which a meeting room is not established for a public health event, the aggregator sub-module 284 ensures that all related data are properly identified and stored in a common file.

FIG. 3C shows selected architectural features of message broker 255, and its connection to other components of the architecture 200. The message broker 255 receives inputs from a variety of components, including, but not limited to the ESB 220. For example, the ESB 220 may provide an initial alert notice, based on the processed data from a specific information source, that a public health event may exist. Message data synchronization sub-module 257 compares this alert with other automated or manual alerts to determine if a new notification, or alert, is justified. For example, an alert received at 1 p.m. EST may simply duplicate information contained in an alert received five minutes earlier. Alternatively, the message broker 255 may be processing an outgoing alert at the same time as a new alert is received. Rather than duplicating alert notifications, the sub-module 257 simply combines any information from outstanding alerts so that a single notification issues. Messaging algorithm 259 provides a triage function, or other function, so that the highest priority alert notification addressees are notified first (note that the notifications may be provided to human users and to other computer systems, news media, etc.). Supervisor and control sub-module 253 determines the mode(s) of notification, such as email, automated telephone call, or both, for example. For call and emails, multiple addresses may be used. The sub-module 253 may also monitor the communications path for a read response. If such a read response is not received within a specified time, the sub-module 253 may employ other means to communicate with the designated individual or system. For example, failure to get a read back from a primary individual may cause the sub-module 253 to issue a message to a secondary individual stating that the primary individual has not been notified.

Figure 4:
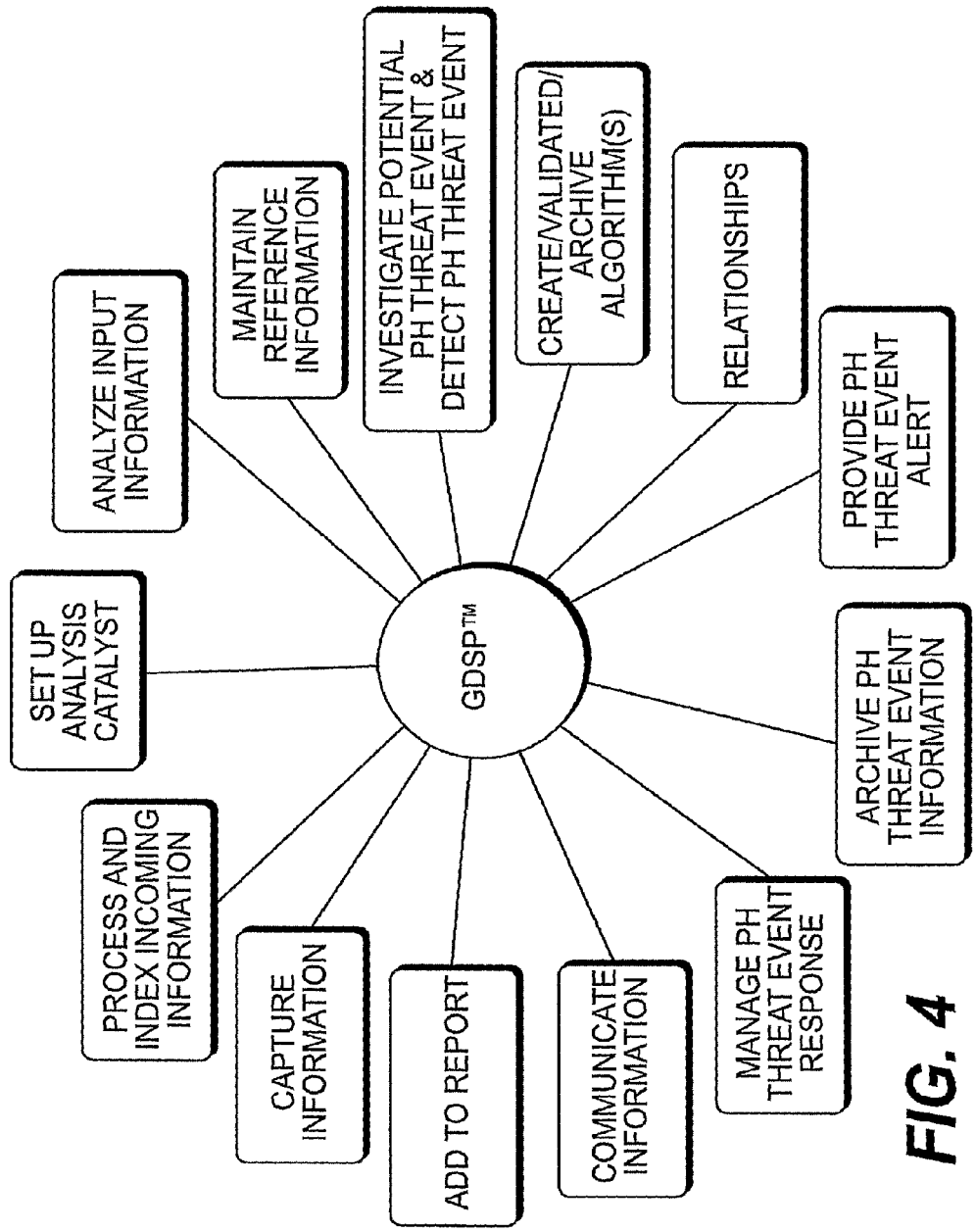
FIG. 4 is a conceptual model of the GDSP™ functions.

FIG. 4 is a conceptual model of the GDSP™ functions. Starting with the function, "Capture Information," and working clockwise, provides an approximate temporal relationship among the functions. Thus, once the GDSP™ 100 captures information, that information is processed and indexed, analyzed, investigated, and archived. Along the way, analysis of the information may lead to alerts that a potential public health threat has been identified and detected.

FIGS. 5A-5E are flowcharts illustrating exemplary GDSP™ processes. Because of the data intensive nature of these processes, one or more computing devices, suitably programmed to execute GDSP™ code, are used to complete the processes.

Figure 5A:
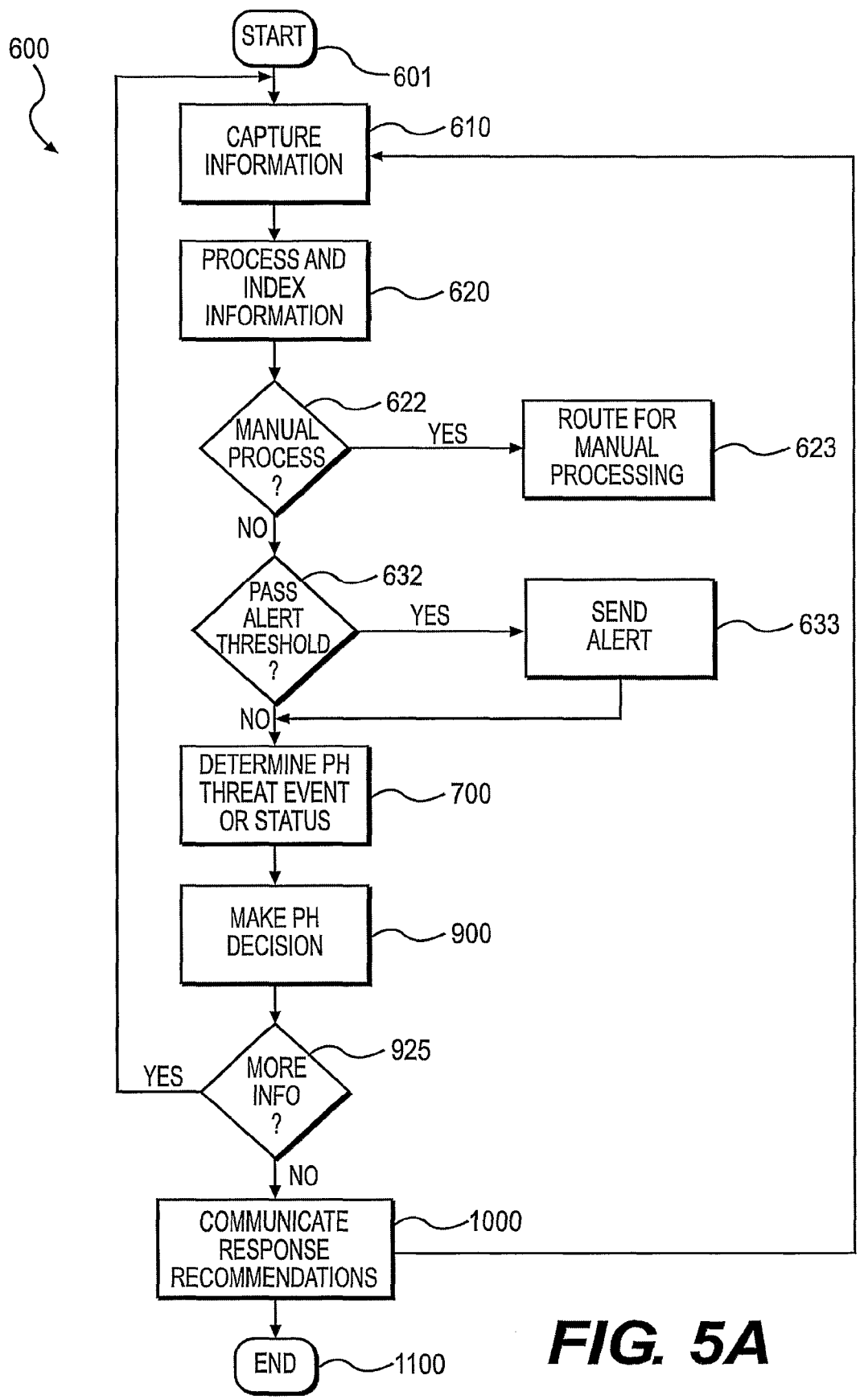
FIGS. 5A-5E are flowcharts illustrating exemplary GDSP™ processes.

FIG. 5A is a flowchart illustrating an overall GDSP™ process 600. The process 600 begins with block 601, wherein public health information is available to the GDSP™ 100 shown in FIG. 2. In block 610, information from various sources 150, 170 arrives at the GDSP™ 100, and the process of data entry and analysis begins in the ESB 220 and the processing components 250 of the GDSP™ architecture 200 shown in FIG. 3A. The information sources include other surveillance and biosurveillance systems as well as non-surveillance systems such as clinical systems, lab systems, reporting systems, media reports, blogs, articles, and other sources. Some of these sources may push information to the GDSP™ 100; for example the GDSP™ 100 may subscribe to certain information sources. Other sources may be queried by agents of the GDSP™ 100, and may provide information in response to these queries. In general, the GDSP™ 100 receives information on a regular, periodic basis.

Next, in block 620, the GDSP™ 100 processes and indexes the incoming information. Since incoming information is received on a regular, periodic basis, the processing and indexing of block 620 also occurs on a regular, periodic basis. However, the GDSP™ 100 may buffer certain incoming information before executing block 620. In processing and indexing the incoming information, the GDSP™ 100 develops a consistent set of meta-data to describe each information source, or document, and to allow indexing the derived meta-data to the entire information source or document. Thus, not only is a database of meta-data created, but the entries in the meta-data database are indexed to the original information source or document, and the original information source or document is later archived in such a manner as to be retrievable for later review and analysis if needed. The result of the processing and indexing is a consistent set of meta-data that the GDSP™ algorithms can use to identify anomalies, such as outbreaks, pandemics, epidemics, or bio-terrorism acts, for example, and to support the investigation, by GDSP™ users, of potential threats.

To develop the consistent set of meta-data, unstructured data such as email, blogs, and RSS feeds are parsed by unstructured text and natural language processors to extract the meta-data, and may be broken down into smaller individual event reports for clarity. Then the extracted meta-data are then tagged to indicate data quality.

Once tagged, the meta-data may be routed, blocks 622, 623 to system administrators for manual processing. The decision to route for manual processing may be based on the content of the meta-data (e.g., the source, time and date), a possible relationship to an existing public health event, or all information is routed for manual processing, for example. Video and audio media is initially translated into text and then processed in the same manner as unstructured data.

Finally, once the meta-data are extracted, agents within the GDSP™ 100 may review the meta-data, and, based on thresholding algorithms, provide alerts, blocks 632, 633 to specific portions of the GDSP™ 100, to systems linked to the GDSP™ 100, and to individual GDSP™ users (e.g., the users 140—see FIG. 2).

In block 700, the GDSP™ 100 is used to determine if a public health event exists, or to update an existing event. That is, the processed data may indicate a new potential public health threat, or may relate to an existing potential or established (declared) public health event. Processing to determine the existence of such an event is described in detail with respect to FIGS. 5B and 5C. If a public health event is deemed to exist, or if the status of the event has changed by a significant enough amount, the process 600 proceeds to block 900, and a public health decision is rendered. This decision has both automated and manual (i.e., human intervention) aspects: specifically, automated and manual event notifications. One additional aspect of the processing associated with block 900 is to seek additional information before concluding that a public health event definitely exists, block 920. The processing associated with block 900 will be described in detail with respect to FIG. 5D. If a public health event exists, or has changed sufficiently, then the GDSP™ 100 supports various communications and response actions, block 1000. Should the declared public health event continue to exist, then the process 600 returns to block 610, and additional information related to the ongoing event is captured. Using many of the same functions of the initial public health decision process 900, effectiveness of response actions are monitored and evaluated with possible new response recommendations being generated. Finally, once the communications and response processing has been completed, and the public health threat eliminated, or at least substantially reduced, the various information, analysis, and reports are archived, and then the processing ends, block 1100, as to that specific public health event.

Figure 5B:
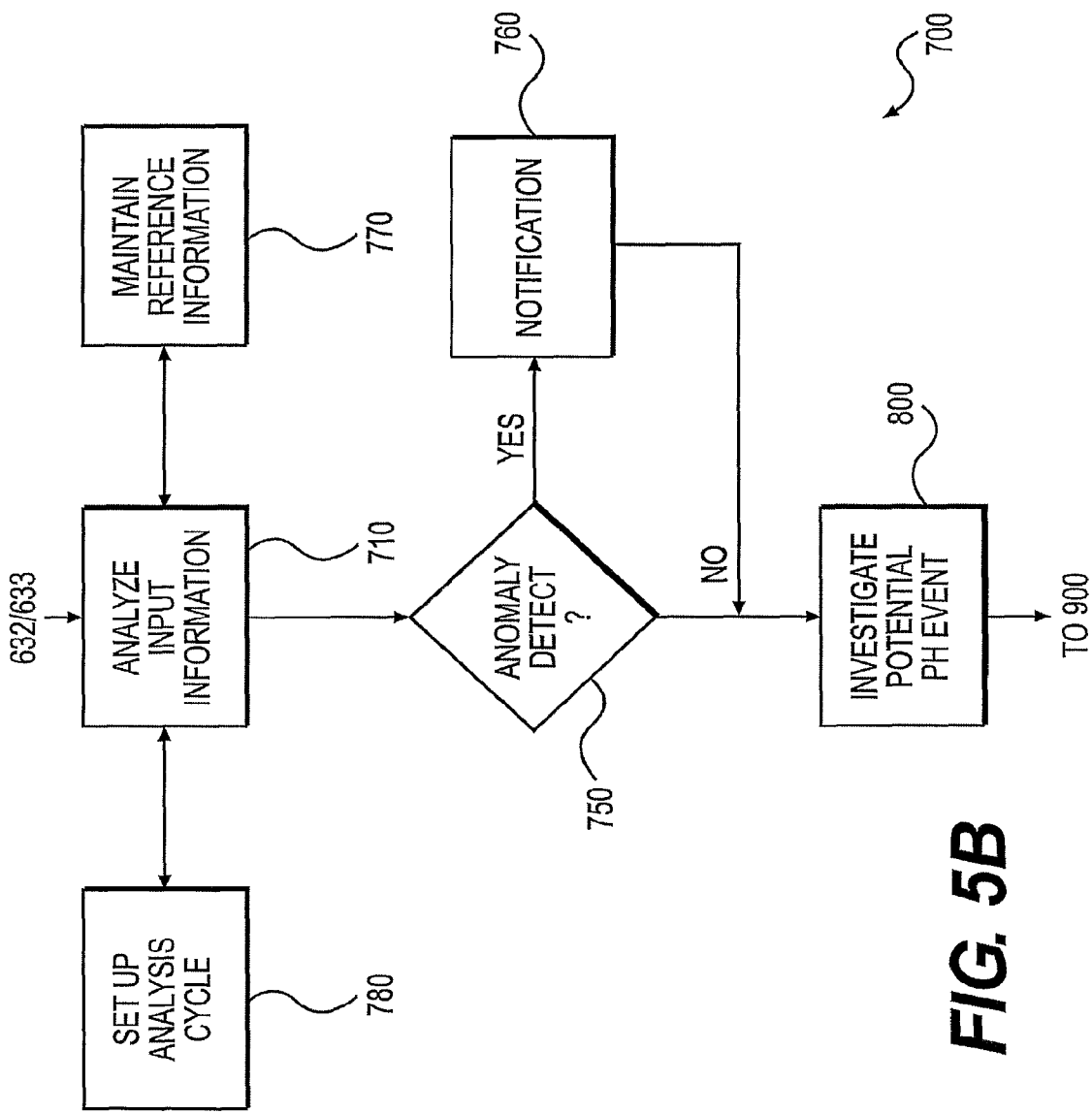

Returning to the processing associated with block 700, FIG. 5B shows the overall process associated with determining if a public health event exists. In block 710, the meta-data extracted from the input information is processed in the GDSP™ 100 using various detection algorithms for automated anomaly detection. Such detection algorithms may include searches for keywords, relationships between location of a data source and the time and date of the reported source, whether reported event involves a human patient, number of human patients involved, etc. The detection algorithms may be pre-existing, or may be newly generated or modifications of an existing algorithm, depending on the nature of the processed meta-data, the underlying meta-data source, and the decisions of the GDSP™ administrators.

If the detection algorithms indicate an anomaly exists, block 750, then in block 760, notifications may be sent to associated systems and human users of the GDSP™ 100. These notifications may be made widely available to encourage general investigation and assessment, but are precursors to official GDSP™ alerts, which, as will be described later, require validation and authorization from an accredited GDSP™ user.

Associated with the process of analyzing the input meta-data are processes to Maintain reference information, block 770, and to set up an analysis cycle, block 780. In maintaining reference information, block 770, the GDSP™ 100 provides users with reference information, such as disease(s)/conditions(s) of interest lists, disease indicators, data sets to include in the analysis, and terminology lists and mappings. This process includes the set up of modeling parameters used as reference information for block 710 in both a default mode and a user-controlled mode. That is, for example, the automated processes of block 710 may execute using default parameters, which a GDSP™ user may choose to override.

In block 780, the GDSP™ 100 may use a standard interface(s) to set the parameters of the analysis cycle (e.g., in block 710) for various phases of a public health event. This process also provides the ability to set thresholds that serve as the dividing line between various public health event phases (e.g., disease outbreak and disease spread).

Whether or not an anomaly is determined at block 750, processing proceeds to block 800, wherein the potential for a public health event is evaluated.

Figure 5C:
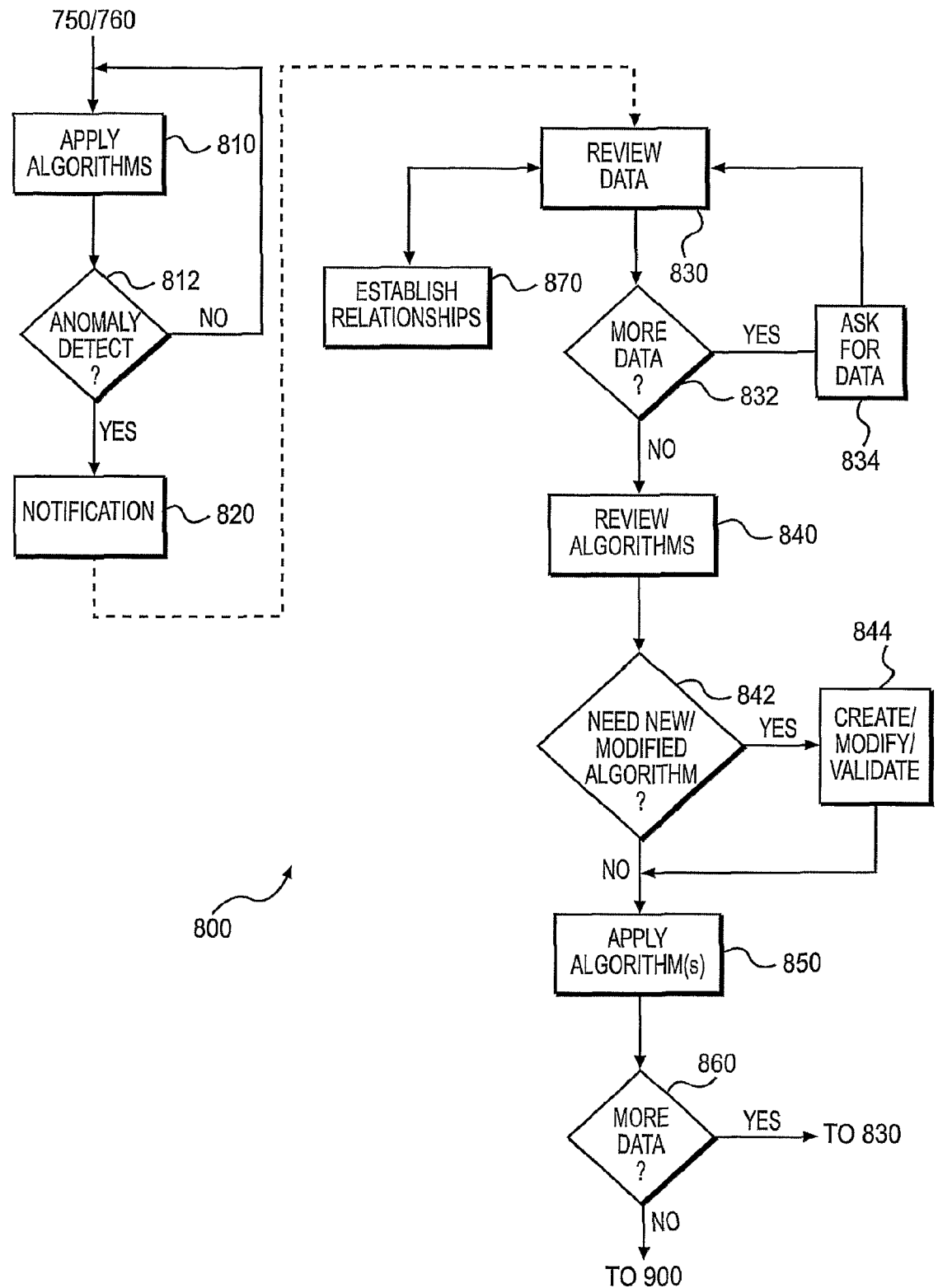

FIG. 5C illustrates the steps associated with the process of detecting and investigating a potential public health event, block 800. In FIG. 5C, some steps may be performed manually, some automatically, and some may be both automated and manual. In block 810, the GDSP™ 100 applies automated detection algorithms to the input information to determine if an anomaly exists. The processing in block 810 may thus be viewed as a continuation of the automated anomaly detection process executed in block 710. If an anomaly is detected, block 812, then the process 800 moves to block 820. Note that the anomaly detection, block 812, is in addition to the anomaly detection of step 750. This additional anomaly detection takes account of the fact that additional and "fused" information sources may present a somewhat different picture of the threat to public health, and also the fact that GDSP users/analysts may add information/ analyses to that already associated with the public health event at issue (for example, through use of the collaborative team room). If no automated anomaly is detected, processing may return to block 810, and as additional meta-data are provided, the automated detection algorithms are re-executed. In block 820, if notifications of the anomaly have not already been made, then such notifications are sent.

Either in parallel with the automated anomaly detection processing and notification of blocks 810-820, or following the notification of block 820, the process 800 may move to block 830, and a GDSP™ user/analyst begins a detailed investigation into the potential public health event. The data review of block 830 may involve opening or establishing a collaborative team room (i.e., a virtual meeting room) in which appropriate GDSP™ users can view data associated with the potential public health event, contribute analyzes, and provide additional information. The team room may be made to persist from the creation of the team room until its associated (potential or actual) public health event is over. Using the team room, and various tools (e.g., global mappings, geospatial and temporal graphing devices, data mining, reporting mechanisms, security mechanisms, and various detection and analysis algorithms) provided by the GDSP™ 100, the GDSP™ user/analyst can organize information into a single coherent picture and provide situational awareness and insight into the public health event. Furthermore, the GDSP™ users (data providers and/or data consumers) can use this team room throughout the life cycle of the public health event.

After an initial analysis phase, the process 800 moves to block 832, and the GDSP™ user/analyst determines if more information will be needed (which, generally, would be the case). If more information is needed, the GDSP™ user/analyst may communicate that need (block 834) using any conventional means, including emails, telephone calls, etc. The process 800 then returns to block 830. If the initial information provided at block 830 is sufficient, the process 800 moves to block 840, and the GDSP™ user/analyst reviews the various detection/analysis algorithms provided in the GDSP™ 100. If the GDSP™ user/analyst determines that one or more of the algorithms are acceptable, the GDSP™ user/analyst may apply the algorithms (block 850) to the input data associated with the potential public health event. If necessary (block 842), the GDSP™ user/analyst may modify an existing algorithm or generate a new algorithm (block 844). New or modified algorithms may be registered with the GDSP™ 100, but their use may be conditional until verified by an accredited GDSP™ user. Finally, following application of the algorithms, the GDSP™ user/analyst may determine (block 860) that more data are needed before proceeding to process 900, and thus the process 800 may return to block 830.

Associated with the process of detecting and analyzing a potential public health event is process step 870, establishing relationships among the information sources. This process step 870 enables GDSP™ users/analysts to manually connect information sources in the GDSP™ repository 120. This then enables all users to begin to see and communicate (collaborate) about emerging public health threats; for example a news report about the status of a major flood in India and the relationship between this information and that of the spread of a viral infection among the population at risk of this public health threat. This process step 870 automatically captures details about the user who establishes a relationship (or set of relationships) and permits the user to add notes about the relationship. These relationships can be viewed using relationship visualization services. In addition to the manual process, an automated process could be configured upon training of the system over time.

While the steps 830-870 described above are implemented in a computer-aided fashion, in other embodiments, specific steps (e.g., block 870) or all steps may be automated in the GDSP™ 100.

Figure 5D:
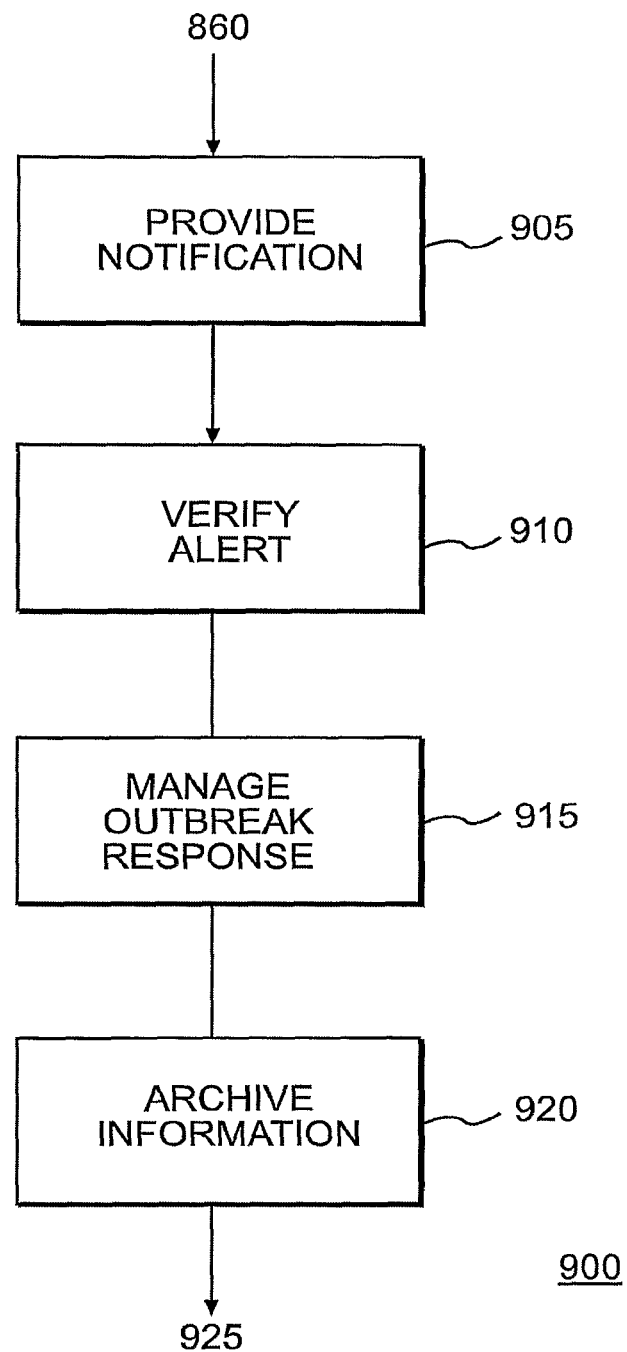

FIG. 5D illustrates the public health decision process 900. The process 900 begins, block 905 when the GDSP™ 100 automatically, or a GDSP™ user/analyst manually, or through a combination of manual and automatic processes, provides notification of a public health event to the appropriate personnel and systems. Various communication methods supported include, but not limited to, email, pager, and telephone. In addition to providing the alert, GDSP™ 100 contains either a list of people, organizations, and systems to be notified and/or uses the resources of an Alerting system that is external to GDSP™ 100. The GDSP™ 100 includes a triage algorithm for an alerting and reporting system as well as the contact information, and information requests for a diverse international population.

In the alert process 905 the automated mechanism by which algorithms can be triggered to dispatch and route alerts uses the definition of interest area and assignment of priority. The process 905 also works in conjunction with workflow services to ensure that mandatory polices for release and escalation are observed. The GDSP™ 100 generates alerts when algorithms flag potential health events. An alerting service dispatches alerts to those analysts and organizations who have registered an interest and are accordingly authorized. Workflow policies can be defined within GDSP™ 100 to provide mandatory policy rules for review before release of alerts, and escalation procedures if alerts are not acknowledged in time. Similarly, mandatory policy rules can determine whether alerts are sent prior to being characterized by an analyst. Depending on the output of the algorithm, alerts may be "packaged" with reports or other supplementary data that provide the justification for the alert. Similarly, the alert workflow capability will support review and release of information in a multi-level secure environment.

In block 910, the provided alert is verified. If the alert is credible, the public health event may be characterized in terms of the following:
1. Determine biological agent
2. Route of transmission
3. Source (e.g., release point)
4. Number of individuals affected The characterization will be refined over time, as is demonstrated in the case of the July 1976 outbreak of Legionnaire's disease in Philadelphia illustrated in Table 1.

TABLE 1

Before and After Epidemiological Diagnoses for the July 1976 Outbreak of Legionnaire's Disease in Philadelphia

| Initial epidemiological "working" diagnosis | Final epidemiological diagnosis (six months later) |
| --- | --- |
| Outbreak exists = true<br>Biological agent = the differential diagnosis of infectious pneumonia<br>Source = ?<br>Route of transmission = probably air<br>Set of affected individuals >= 8 cases. | Outbreak exists = true<br>Biological agent = L. pneumophilia<br>Source = water cooling tower, Bellevue Stratford Hotel<br>Route of transmission = air<br>Set of affected individuals = 180 cases |

An associated subscription process provides GDSP™ users/analysts with a set of services that automatically disseminate data. Rather than a user manually looking for information of interest on a periodic basis, the subscription process enables a personalized set of agents constantly looking for information, then generating a notification to the user that data of interest is available, and/or pushing the data to the user. This can be done, for example, using a REST API, RSS, or by manual extraction. The increases a GDSP™ user's productivity through the elimination of constant manual "polling" for data. This process also provides the architectural underpinning for supporting collaborative communities of interest, as well as bidirectional interactions with other sector-specific agencies.

The GDSP™ 100 supports (block 915) response planning and public health event monitoring by managing critical information about confirmed events, such as outbreaks, and communications between international public health professionals for informing actions to limit the spread of the outbreak and mitigate the health, social, and economic impacts of a pandemic. This process provides:

- The use of models (see Analyze Input Information) to make informed inferences about disease spread as the event and event response progresses. These models provide insight into which control strategies might be effective in slowing spread.
- Assist public health and response authorities with the implementation of travel-related and community containment measures through the use of interactive maps that are linked to data about quarantine areas, school and airport locations and closings.
- The GDSP™ 100 can be used to assess the capacity of state and local medical and emergency response systems to meet expected need during a public health threat event. The GDSP™ 100 can also be used to track the availability and location of personnel, areas with patient visit surges, and the beds within healthcare facilities.
- The GDSP™ 100 can facilitate and manage the supply of essential materials to event response sites, transport of laboratory specimens from the field to appropriate diagnostic facilities, the organization of treatment (vaccination) programs, or deployment of teams for disease control.
- Using the notification ability, the GDSP™ 100 can allow public health and response authorities with the ability to request assistance from U.S. federal teams including the Commissioned Corps and Medical Reserve Corps as well as those making ready Federal Medical Contingency Stations.
- The GDSP™ 100 can facilitate the aggregation and communication of speedy treatment effectiveness studies and reports of adverse events following treatments including substance (vaccine, antivirals, etc.) administrations and dispensations.

Finally, in block 920, the GDSP™ 100 provides for information on anomalies detected, decisions made, and actions taken to be archived by the GDSP™ 100. This information is capable of being queried during the event and afterwards for evaluation purposes. Post event-evaluation has much broader applications than only the refinement of algorithms; this evaluation also provides a powerful means for preparedness and response strategies to health threats. Correlation of pre-event data with data recorded during response and recovery provides evidence-based validation for those factors which best minimize the impact of an outbreak. Analysis of data queries and requested reports during an outbreak response will identify data streams that need to be brought into the GDSP™ 100.

Figure 5E:
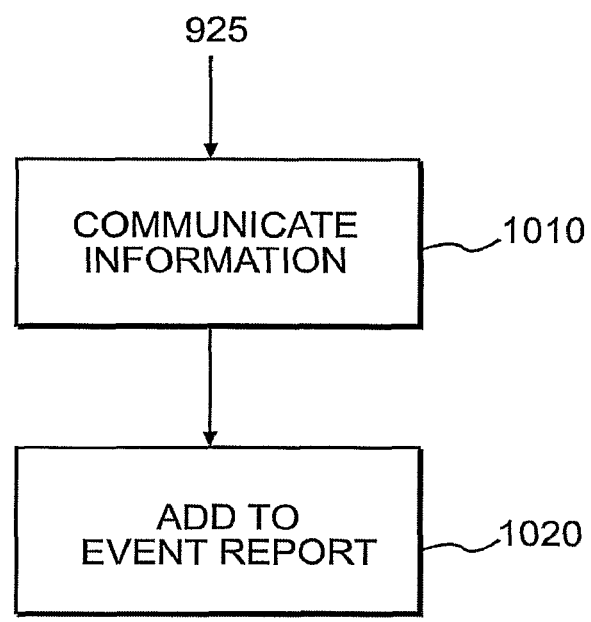

FIG. 5E illustrates the last process steps of the process 600, namely communicate information, block 1010, and adding to an event report, block 1020. The communicate information process 1010 allows a GDSP™ user/analyst to share information in various reporting formats including screen shots, maps, a standard report, and any data used to create the information with applied algorithm(s). Collaborations between analysts and between organizations are supported by the GDSP™ characterization phase. In addition, the GDSP™ 100 supports decision aids and requests for enhanced data collection to provide more analytical capability. Several of the characterization activities involve bidirectional capabilities. The GDSP™ 100 will also start archiving data associated with the potential event. The add to report process 1020 provides a user-driven control to add the GDSP™-presented information to a reporting template in preparation for sending the report.

Figure 6:
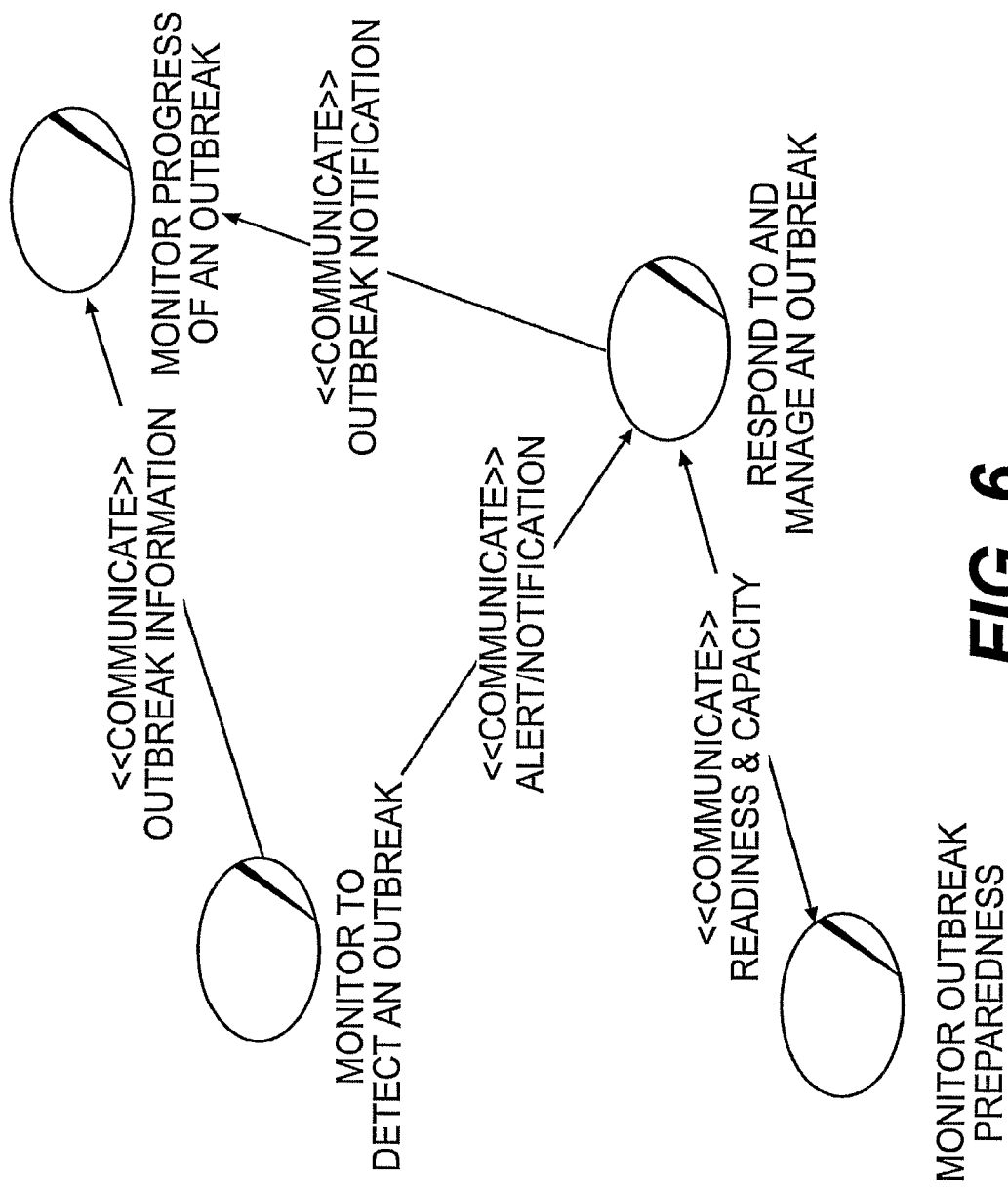
FIG. 6 illustrates various functions of the GDSP™ during a public health event.

FIG. 6 illustrates various phases during a public health event that are included within the GDSP™ 100 method and implementation. These phases include:

Monitor to Detect an Outbreak (Early Event (Outbreak) Detection)
- Monitoring to detect an event monitors the current health of a jurisdiction in order to find or identify event of concern to the Public Health. This phase includes all the features and functions needed to collect data from source systems, including organizations and people, consolidate the collected information into a coherent picture, and present the information so that a knowledgeable person, generally an epidemiologist, can interpret the presented information in order to detect an event.

Monitor Progress of an Outbreak
- This phase tracks the progress of an event by monitoring both the effect of any event investigations and responses as well as continuing to monitor the current situation. Since the Monitor to Detect an Event also monitors the current situation, this phase includes the features and functions of the Monitor to Detect an Outbreak phase. In order to monitor the progress of an event, the Detect an Event phase will involve the communication of all known or suspected event information to the Monitor the Progress of an Event business phase.

Monitor Outbreak Preparedness
- This phase involves continual monitoring by an agency, jurisdiction, or organization in order to respond to an event. This phase involves monitoring emergency response planning, training, and overall response capacity.

Respond to and Manage Response to an Outbreak
- Event response involves many teams across many disciplines and with many purposes.
- In order to be effective, event response must be managed in a clear, effective manner. This phase provides for initiating an event response and managing the response including cross-jurisdictional responses.

Table 2 summarizes these phases.

TABLE 2

GDSP ™ Public Health Event Phase Summary

| GDSP ™ Processes | Monitor to Detect an Outbreak | Monitor Progress of an Outbreak | Manage Outbreak Response | Monitor Outbreak Preparedness |
|---|---|---|---|---|
| Capture Information | X | X | X | X |
| Transform Incoming Information | X | X | X | X |
| Analyze Input Information | X | X | X | X |
| Maintain Reference Information | X | | | |
| Create/Validate/Archive Algorithm(s) | X | X | | |
| Set up Analysis Cycle | X | X | | |

TABLE 2-continued

GDSP ™ Public Health Event Phase Summary

| GDSP ™ Processes | Monitor to Detect an Outbreak | Monitor Progress of an Outbreak | Manage Outbreak Response | Monitor Outbreak Preparedness |
|---|---|---|---|---|
| Investigate Potential PH Threat Event & Detect Potential PH Threat Event | X | X | | |
| Provide PH Threat Event Alert | X | | | |
| Manage Response to PH Threat Event | | X | | |
| Archive PH Threat Event Information | | X | | |
| Communicate Information | X | X | X | X |
| Add to Report | X | X | X | X |

As can be seen from Table 2, certain of the GDSP™ functions illustrated in FIG. 4, and described in FIGS. 5A-5E, are executed by the GDSP™ 100 during each of the public health event phases, while others relate to less than all the phases.

FIG. 7 is a sample alert feed used with the GDSP™ 100. As shown in FIG. 7, the alert is a formatted XML message that identifies the location of the potential public health event, and specific information relating to the number of victims. Other alerts may be formatted in differing fashions, and may contain additional information regarding the event.

Figure 8:
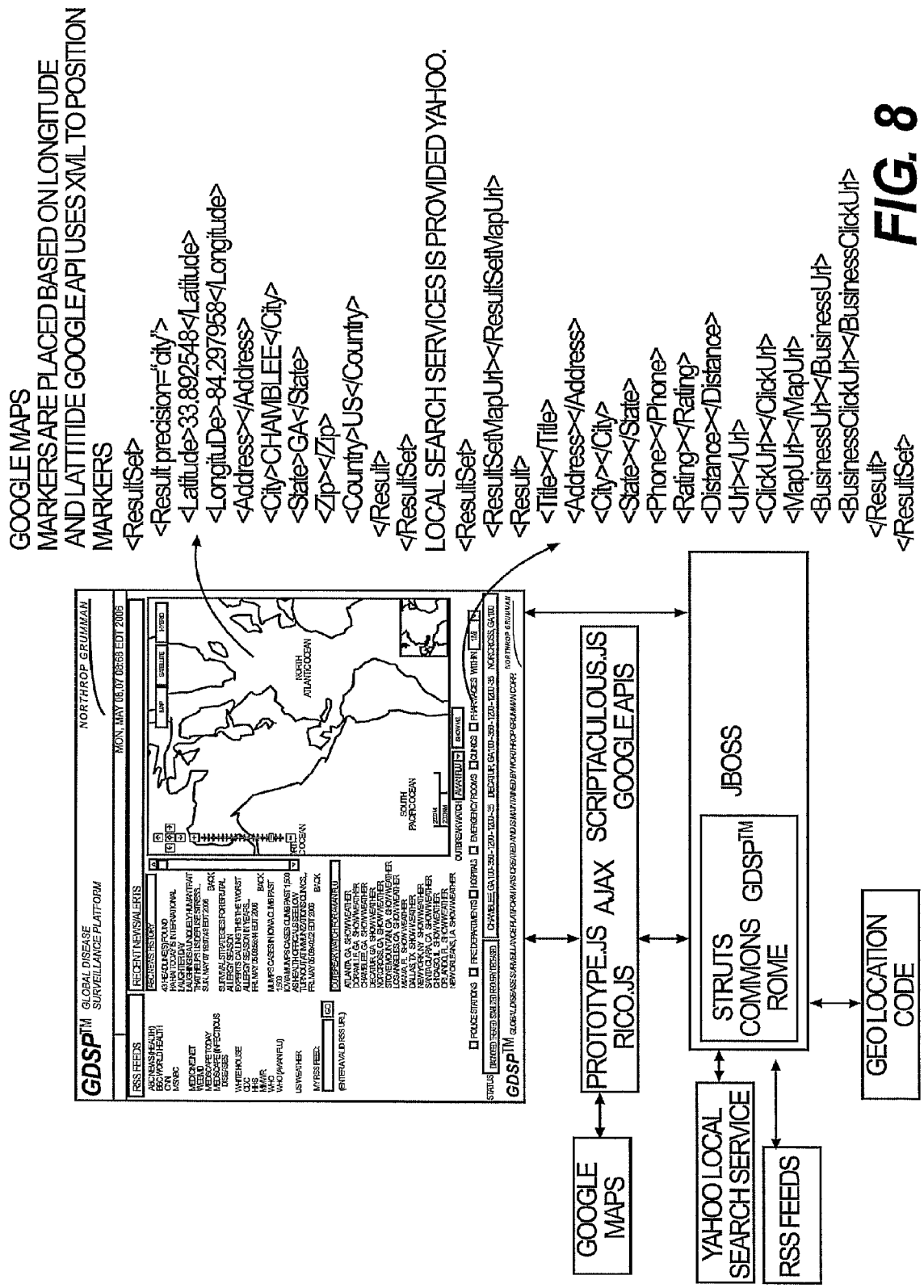

FIGS. 8-20 are user interfaces that illustrate features and functions of the GDSP™ 100 of FIG. 2. FIG. 8 show the overall usage on the components by the browser (295). The browser 295 interacts with the AJAX components (258) and the overall processing components 250 to communicate requests to Google Map (243) and Yahoo services (291, 293, 295). In addition the browser 295 can call the processing components 250 directly.

FIGS. 9-20 show the visual representation of what a GDSP™ user will be able to perform once the GDSP™ 100 is displayed on the browser 295, for example. For example, a Google Map 245 is displayed on the browser 295. The user can interact with the map 245 through the use the AJAX utility 258 thereby adding markers such as traffic (293) and places (295). High level map technology integration can be viewed in FIGS. 8-14 while layer integration such as hospital, fire department, police station and or patient information can be viewed in FIGS. 15-17, with both integration layers providing situation awareness.

The portal 110 also visualizes structured (232) and unstructured data (234) using the browser (295). In this scenario the GDSP™ users can display data related to a particular disease/condition or display outbreak/crisis related information such as news and video feeds, and be able to drill in and drill back out in order to maintain a situation awareness and if needed request additional supporting information. The links/cache information is stored in the GDSP™ store 280.

Figure 18:
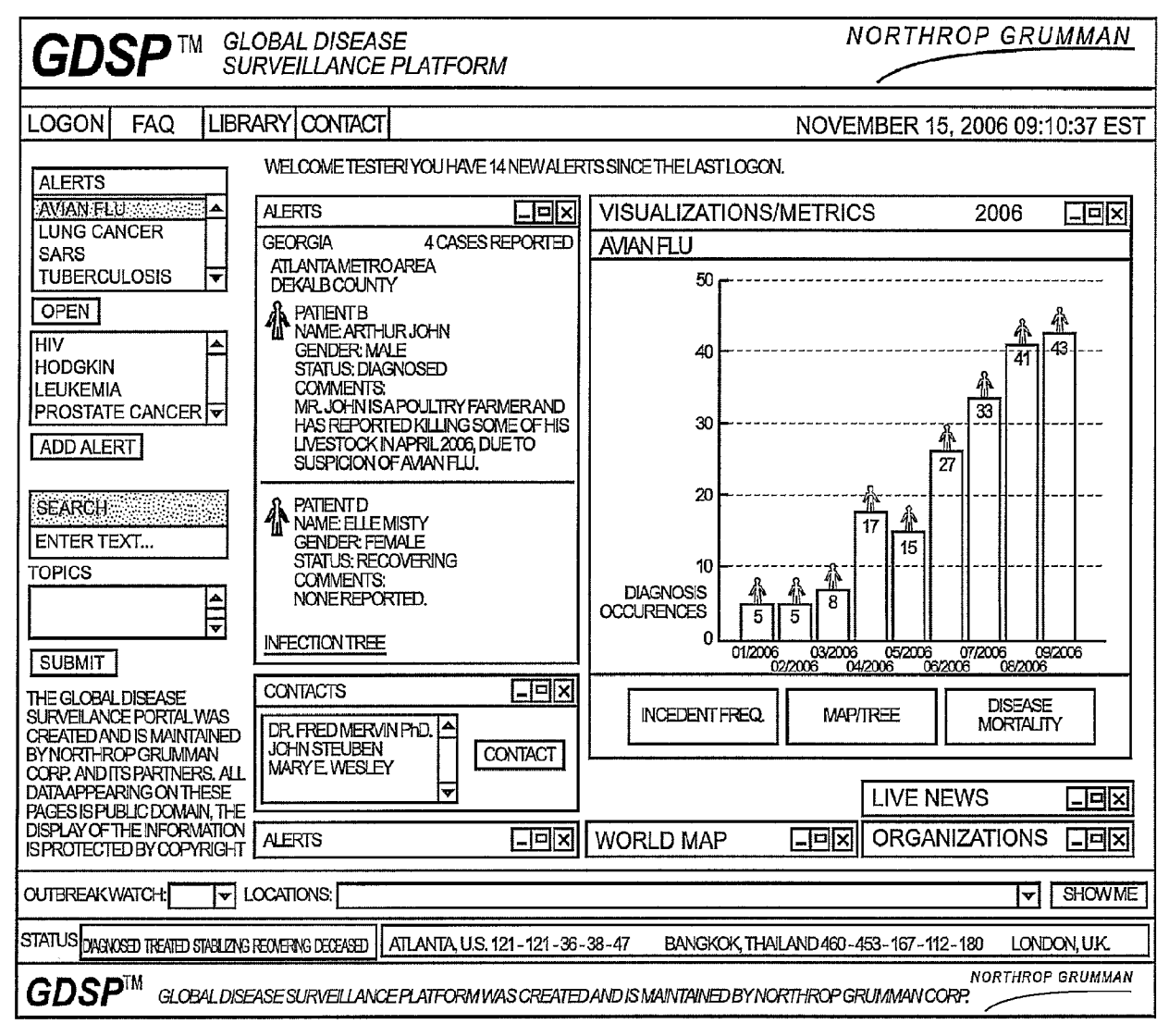
Figure 19:
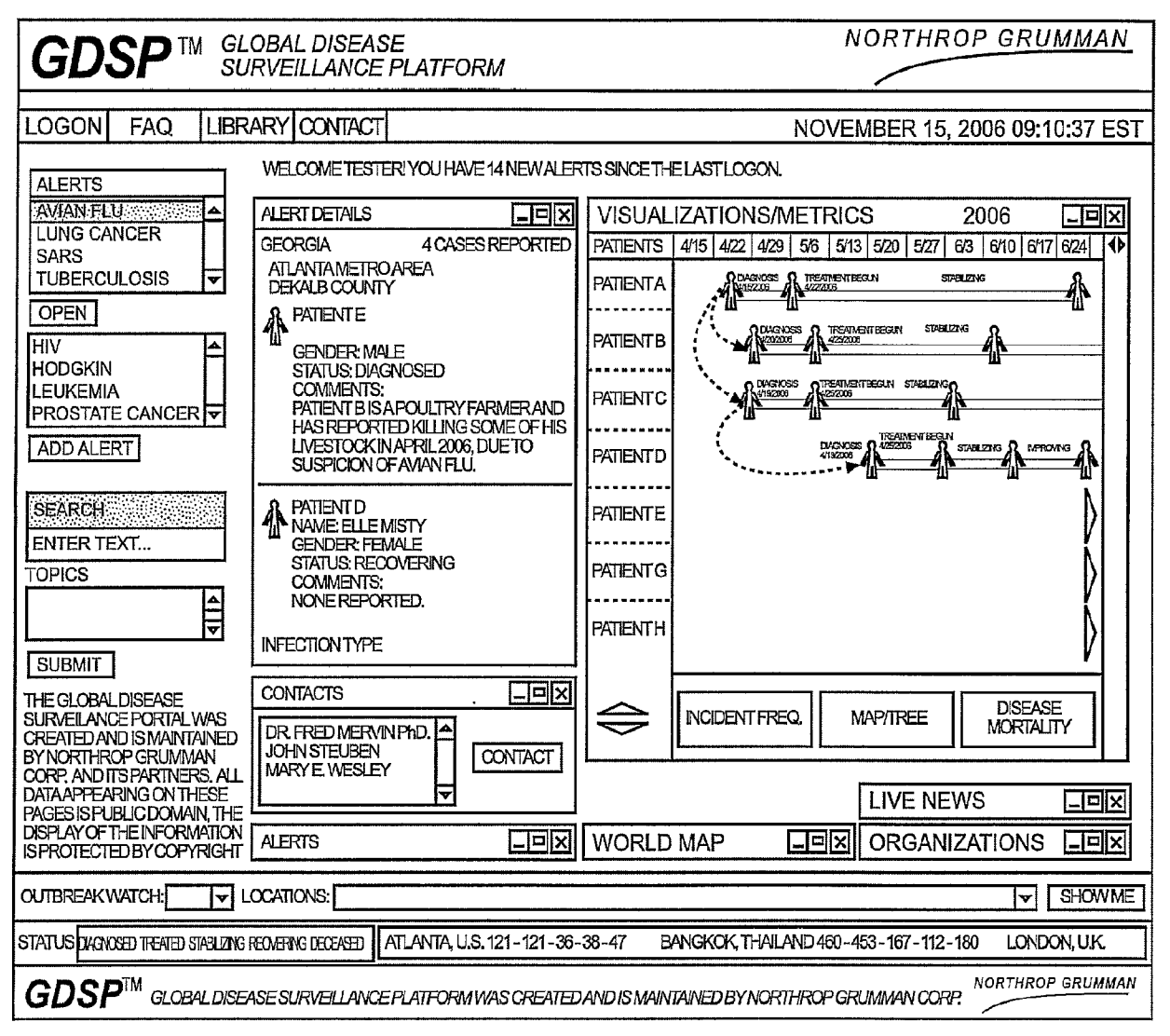

GDSP™ analytics are displayed in FIGS. 18-19. In this case, GDSP™ user can use the browser 295 to drill down by using services provided by processing components 250. Algorithms can be shared and built collaboratively across users or agencies and cross-validated on different populations, scenarios, conditions, contexts, and/or geographic regions.

Figure 21:
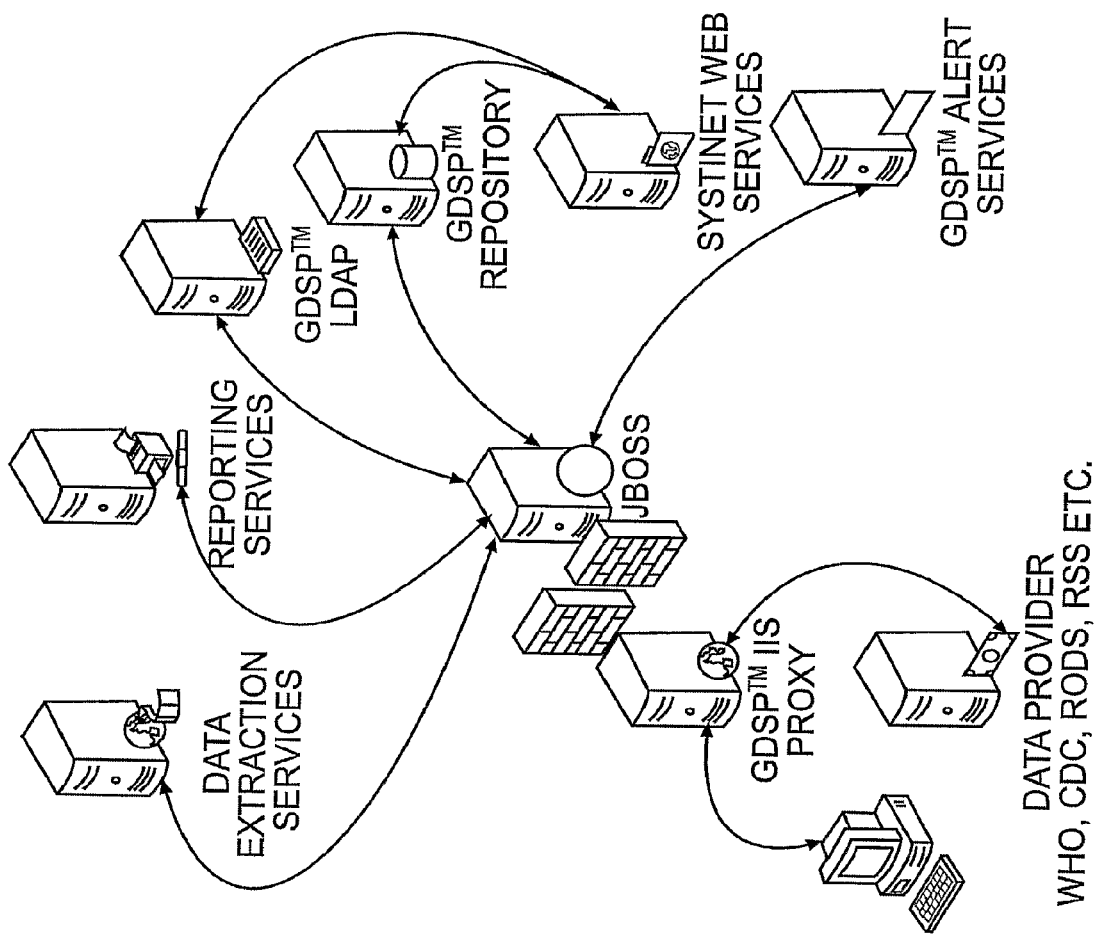
FIG. 21 illustrates a computing network for implementing the GDSP™.

FIG. 21 illustrates an exemplary computer network for implementing the GDSP™ 100.

The invention claimed is:

1. A global disease surveillance platform for identifying, determining, and analyzing potential public health events and monitoring responses thereto, comprising:
   an interface configured by computer-executable instructions to:
      receives external information feeds comprising structured and unstructured data;
      transform the structured and unstructured data into a schema consistent with a schema of the platform;
      extract meta-data from the structured and unstructured data, index the meta-data, and relate the meta-data back to the structured and unstructured data; and
      store the structured data, the unstructured data, and the meta-data in a storage device;
   an external services module that provides services to facilitate the responses; and
   a platform processor coupled to the interface and the external services module and configured by computer-executable instructions to:
      analyze the meta-data in relation to one or more thresholds and to trigger transmission of a public health alert by an alert module; and
      identify, evaluate, tag, and correlate the structured data, the unstructured data, and the corresponding meta-data to produce a data file related to a specific public health event; and
      provide real-time user access to the data file for pre-planning, detection, and response to the public health event.

2. The platform of claim 1, wherein the external services comprise geo-spatial services.

3. An apparatus for managing phases of a public health event, the apparatus including one or more suitably programmed computing devices, the apparatus comprising:
   an interface configured to receive structured and unstructured data from one or more external data sources and further comprising:
      a data transformation module that transforms data from the structured and unstructured data sources into a schema consistent with a schema of the apparatus, and
      a data classification module that extracts meta-data related to the structured and unstructured data and creates an index of the meta-data back to the meta data's structured or unstructured data;
   a data store coupled to the interface, wherein the indexed meta-data and the structured and unstructured data are stored;
   a processing component coupled to the interface, comprising:
      an analysis module configured to analyze the meta-data in relation to one or more thresholds and to trigger transmission of a public health alert by an alert module; and
      access modules configured to provide real-time user access to the structured and unstructured data, and to the corresponding meta-data for pre-planning, identification, detection, and response to the public health event.

4. The apparatus of claim 3, further comprising external services coupled to the processing component, wherein the processing component is configured to receive geo-spatial information and to populate one or more geo-spatial products with the extracted meta-data, wherein the populated geo-spatial products provide visual and temporal displays of progress of the public health event, including indications of populations at risk from the public health event, and wherein the geo-spatial products allow monitoring of effectiveness of response actions.

5. The apparatus of claim 4, wherein the populated geo-spatial products further provide visual indication of locations of public health response assets.

6. The apparatus of claim 3 wherein the analysis module is further configured to trigger a notification of an event or anomaly to one or more users of the apparatus by the alert module.

7. The apparatus of claim 6, wherein the alert module incorporates a triage algorithm for notification of the users.

8. The apparatus of claim 3, wherein the index provides retrieval of structured and unstructured data, corresponding to the indexed meta-data, from the data store, for further analysis.

9. The apparatus of claim 3, further comprising a virtual meeting room, wherein analysis of the public health event-related data are displayed and information related to the public health event are received from users of the apparatus.

10. A method for managing a response to a public health event during an entire life cycle of the event, the method executed on one or more computing devices including at least one processor, the method comprising:
    receiving information contained in one or more structured and unstructured data sources;
    initially processing the information, comprising:
        extracting, using the at least one processor, meta-data from the data sources, wherein the meta-data are linked to their corresponding data source,
        transforming, using the at least one processor, the extracted meta-data,
        classifying, using the at least one processor, the transformed meta-data to create indexed meta-data, and
        storing, using a storage device, the indexed meta-data and their corresponding data source, wherein the indexed meta-data allows retrieval of the corresponding data source; and
    analyzing, using the at least one processor, the meta-data to determine if a threshold value indicative of a public health event has been exceeded, wherein if the threshold has been exceeded,
        providing an initial public health event alert, and
        continuing, using the at least one processor and the storage device, to collect, process, and analyze information to allow management of the response.

11. The method of claim 10, further comprising:
    applying one or more detection algorithms to the meta-data to determine the extent of the public health event and to prepare and subsequently manage the response to the public health event; and
    archiving information related to the public health event.

12. The method of claim 10, wherein the public health event is one of acute, mild, and chronic conditions, wherein the public health event affects one or more of humans, animals, and the environment, and wherein the public health event is caused by one or more of natural, technological, man-made, and bio-terrorism mechanism.

13. The platform of claim 1, wherein the unstructured data comprises data selected from the group consisting of audio, video, blog, body of an email, and word processor document.

14. The apparatus of claim 3, wherein the unstructured data comprises data selected from the group consisting of audio, video, blog, body of an email, and word processor document.

15. The method of claim 10, wherein the unstructured data source comprises an item selected from the group consisting of audio source, video source, blog, body of an email, and word processor document.

16. The platform of claim 1, wherein the analysis module is configured to analyze the meta-data using at least one of the following algorithms: moving average, CuSum with EWMA, recursive least squares, wavelet, cluster detection, Bayesian analysis, and heuristics.

17. The apparatus of claim 3, wherein the analysis module is configured to analyze the meta-data using at least one of the following algorithms: moving average, CuSum with EWMA, recursive least squares, wavelet, cluster detection, Bayesian analysis, and heuristics.

18. The method of claim 14, wherein analyzing the meta-data comprises using at least one of the following algorithms: moving average, CuSum with EWMA, recursive least squares, wavelet, cluster detection, Bayesian analysis, and heuristics.

* * * * *